(12) United States Patent
Valerio et al.

(10) Patent No.: US 6,472,212 B1
(45) Date of Patent: *Oct. 29, 2002

(54) METHODS AND COMPOSITIONS FOR GENETICALLY MODIFYING PRIMATE BONE MARROW CELLS

(75) Inventors: Domenico Valerio, Leiden; Victor Willem Van Beusechem, Amsterdam, both of (NL)

(73) Assignee: Introgene B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 08/820,479

(22) Filed: Mar. 18, 1997

Related U.S. Application Data

(63) Continuation-in-part of application No. 08/211,342, filed as application No. PCT/NL92/00177 on Oct. 5, 1992, now Pat. No. 5,612,206.

(30) Foreign Application Priority Data

Oct. 4, 1991 (NL) ............................................. 9101680

(51) Int. Cl.$^7$ .......................... C12N 15/86; C12N 5/00; C12N 15/63; C07H 21/04
(52) U.S. Cl. ....................... 435/456; 435/455; 435/373; 435/366; 435/372; 435/320.1; 536/23.1; 536/23.2; 536/23.5; 536/24.1
(58) Field of Search ................................ 435/373, 325, 435/363, 366, 320.1, 455, 456, 372; 536/23.1, 23.2, 23.5, 24.1

(56) References Cited

U.S. PATENT DOCUMENTS

| 5,198,423 A | | 3/1993 | Taguchi ........................ 514/12 |
| 5,534,423 A | * | 7/1996 | Palsson et al. ............... 435/456 |
| 5,612,206 A | * | 3/1997 | Valerio et al. ............... 435/456 |
| 5,654,185 A | | 8/1997 | Palsson .................... 435/235.1 |
| 5,686,278 A | | 11/1997 | Williams et al. ............. 435/456 |
| 5,686,279 A | | 11/1997 | Finer et al. .................. 435/457 |

FOREIGN PATENT DOCUMENTS

| WO | WO 97/00326 | 1/1997 |

OTHER PUBLICATIONS

Nimgaonkar, M. et al. Long term expression of the glucocerebrosidase gene in mouse and human hematopoietic progenitors. Leukemia 9:S38–S42, 1995.* van Zeijl, M. et al. A human amphotropic retrovirus receptor is a second member of the gibbon ape leukemia virus receptor family. Proc. Natl. Acad. Sci. 91:1168–1172, 1994.* von Kalle, C. et al. Increased gene transfer into human hematopioetic progenitor cells by extended in vitro exposure to a pseudotyped retroviral vector. Blood 84:2890–2897, 1994.*

Moore, K.A. et al. Stromal support enhances cell free retroviral vector transduction of human bone marrow long term culture initiating cells. Blood 79:1393–1399, 1992.*

Sutherland, H.J. et al. Characterization and partial purification of human marrow cells capable of initiating long term hematopoiesis in vitro. Blood 74:1563–1570, 1989.*

Bodine, D.M. et al. Development of a high titer retrovirus producer cell line capable of gene transfer into rhesus monkey hematopoietic stem cells. Proc. Natl. Acad. Sci. 87:3738–3742, 1990.*

Roberts, R.A. et al. Metabolically inactive 3I3 cells can substitute for marrow stromal cells to promote the proliferation and development of multipotent haemopoietic stem cells. J. Cell. Physiol. 132:203–214, 1987.*

Markowitz et al, *Journal of Virology* (Nov. 1988) 167(1):400–406.

van Beusechem et al, *Journal of Experimental Medicine* (Sep. 1, 1990) 172(3):729–36.

Markowitz et al, *Journal of Virology* (Sep. 1988) 62(9):3388–3398.

Markowitz et al, *Journal of Virology* (Apr. 1988) 62(4):1120–1124.

* cited by examiner

Primary Examiner—Dave T. Nguyen
Assistant Examiner—Quang Nguyen
(74) Attorney, Agent, or Firm—TraskBritt

(57) ABSTRACT

A method is provided for genetically modifying primate bone marrow cells, comprising isolating bone marrow cells from a primate and, by means which enhance the local concentration of retroviral contacting the isolated bone marrow cells to cells that produce a recombinant amphotropic retrovirus with a genome based on a retroviral vector that contains the genetic information to be introduced into the bone marrow cells. Recombinant amphotropic retrovirus-producing cells, suitable for use in this method also are provided, as are genetically modified primate bone marrow cells with the capacity for regeneration in vivo.

14 Claims, No Drawings

METHODS AND COMPOSITIONS FOR GENETICALLY MODIFYING PRIMATE BONE MARROW CELLS

CROSS-REFERENCE TO RELATED APPLICATIONS

This application is a continuation-in-part of U.S. Ser. No. 08/211,342, filed on Jun. 21, 1994, now U.S. Pat. No. 5,612,206, which is the antional application of PCT/NL 92/00177 filed Oct. 5, 1992, which claims foreign priority benefits under title 35, United States Code, Section 119, to Foreign Application No. 9101680, the Netherlands, filed Oct. 4, 1991 which disclosures are incorporated herein by references.

FIELD OF THE INVENTION

The invention concerns the field of gene therapy and more particularly relates to a method for genetically modifying primate bone marrow cells so that they have the capacity to regenerate in vivo, and to cells that produce recombinant retroviral vectors that can be used in such a method. The method is exemplified by the use of means which enhance the local concentration of retroviral particles derived from the murine leukemia virus in the vicinity of target primate stem cells.

BACKGROUND

Developments in the field of molecular biology have led to a better understanding of the genetic basis underlying the development of a large number of disorders. It is expected that the genes which are associated with the diseases that occur most frequently will have been identified, cloned and characterized before the end of this century.

So far, molecular genetics has contributed to medicine by the development of diagnostic tools and methods and the biotechnological production of pharmaceuticals. It may be expected, however, that it will also be possible to use the increasing knowledge of genetics for an essentially new therapeutic treatment, the so-called gene therapy. The purpose of gene therapy is to treat disorders by genetically modifying somatic cells of patients. The uses of gene therapy are not limited to hereditary disorders; the treatment of acquired diseases is also considered to be one of the possibilities. Although this field of study is still in a preliminary stage and must be developed, therapeutic possibilities are in the distance which can drastically improve medicine in the future (Anderson, (1984) *Science* 226:41 0; Belmont and Caskey, (1986) in Gene Transfer, R. Kucherlapati, eds, Plenum press, New York and London, P. 411; and Williamson, (1982) *Nature* 298:416.)

An important cell type for gene therapy purposes is the so-called hematopoietic stem cell which is the precursor cell of all circulating blood cells. This stem cell can multiply itself without losing its differentiating ability. In adult animals most stem cells are situated in the bone marrow. Very infrequently stem cells also start to circulate in the peripheral blood. This can be significantly augmented by treatment with stem cell mobilizing agents, including but not restricted to certain hematopoietic growth factors. In embryos, stem cells are by nature circulating much more frequently. Thus, bone marrow, peripheral blood after stem cell mobilization and embryonic blood, e.g. collected perinatally from the umbilical vein, are useful sources for stem cells. The underlying idea of a gene therapy directed to hematopoietic stem cells is that gene transfer to (a limited number of) stem cells may already be sufficient to replace the entire blood-forming tissue with genetically modified cells for a lifetime (Williamson, (1982) *Nature* 298:416). This would enable treatment not only of diseases that are caused by a (hereditary) defect of blood cells, but also of diseases that are based on the inability to make a certain protein: the modified blood (forming) system could be a constant source of the protein, which could do its work at the places where necessary. It is also possible, with the introduction of genetic material into the blood system, to obtain resistance against infectious agents, to combat cancer, or even to overcome a predisposition to chronic diseases, such as rheumatism or diabetes. Finally, it is noted that in the treatment of some diseases it is to be preferred or necessary that the gene transfer to stem cells is performed on bone marrow cell populations from which certain cell types have been removed. One could for instance consider the use of gene therapy in the treatment of leukemia, in which case there should not occur any gene transfer to the leukemic cells.

One of the conditions for providing of such a bone marrow gene therapy protocol is a technique by which genes can be incorporated into the chromosomes of target cells, in such a manner that those genes are also passed on to the daughter cells and that the desired protein product is produced in those cells. In the invention described here, for this purpose use is made of recombinant retroviruses that carry with them the genes to be introduced and which are capable of delivering them to mammalian cells. They make use of the natural characteristic of retroviruses to integrate efficiently and stably into the genome of the infected cell, but not themselves to cause a productive infection because the retroviruses used are replication-defective and are not contaminated with wild-type viruses (Temin, (1986) in *Gene Transfer*, R. Kucherlapati, eds. Plenum Press, New York, p. 149 and Temin, (1990) *Hum. Gene Ther.* 1:1 1 1). The recombinant retroviruses which are used within the framework of the present invention are derived from viruses with a natural host-specificity that includes primates, or from viruses that can be pseudotyped with a host-specificity that includes primates. Said viruses include, but are not restricted to, murine leukemia viruses (MuLV; Weiss et al., (1984) RNA Tumor Viruses, New York) with a so-called amphotropic or xenotropic host-range, gibbon ape leukemia viruses (GaLV; Lieber et al., *Proc. Natl. Acad. Sci. USA* 72(1975) 2315–2319), and primate lentiviruses.

For the production of recombinant retroviruses, two elements are required: the so-called retroviral vector, which, in addition to the gene (or genes) to be introduced, contains all DNA elements of a retrovirus that are necessary for packaging the viral genome and the integration into the host genome; and the so-called packaging cell line which produces the viral proteins that are necessary for building up an infectious recombinant retrovirus (Miller, (1990), *Hum. Gene Ther.* 1:5).

As the presence of replication-competent viruses in a gene therapy protocol is considered highly undesirable, most modern packaging cell lines are constructed in a way such that the risk of recombination events whereby a replication-competent virus is generated, is minimized. This is effected by physically separating into two parts the parts of the virus genome that code for viral proteins and introducing them into the cell line separately (Danos and Mulligan, (1988) *Proc. Natl. Acad. Sci. USA* 85:6460; Markowitz et al., (1988) *J. Virol.* 62:1120; and Markowitz et al., (1988) *Virology* 167:400).

As the presence of both constructs is essential to the functioning of the packaging cell line and chromosomal instability occurs regularly, it is of great importance for the routine use of such cells in gene therapy procedures that, by means of a selection medium, selection for the presence of the constructs can be provided for. Therefore, these constructs are often introduced by means of a so-called cotransfection whereby both viral constructs are transfected together with a dominant selection marker. The possibility of selection thus provided is certainly not a trivial requirement, considering for instance the observation that we and various other research groups made, that virus-producing cells based on the packaging cell line ψCRIP (Danos and Mulligan, (1988) Proc. Natl. Acad. Sci. USA 85:6460) are not stable. That is to say that they are no longer resistant to the relevant selection media and during cultivation lose their capacity to produce retroviruses. One example, of importance for one of the embodiments of the present invention, is the so-called POC-1 cell line which was produced by us on the basis of ψCRIP cells (Van Beusechem et al., (1990) J. Exp. Med. 172:729) which on account of its instability cannot be used for gene therapy on a routine basis. Therefore, in the invention described here, use is made of packaging cells which, by means of a dominant selection culture, do continue to produce stable virus.

Studies in mice have demonstrated that using amphotropic retroviral vectors, bone marrow stem cells can be provided with a new gene. After transplantation of these modified cells into lethally irradiated mice, the new gene could also be demonstrated for long periods in many different blood cell types of the transplanted animals (Van Beusechem et al., (1990) J. Exp. Med. 172:729).

Previous problems with regard to the non-expression of the newly introduced genes were solved by us by using a retroviral vector in which the expression of the gene of choice, is driven by a retroviral promoter whose expression-specificity has been changed by means of a replacement of the so-called enhancer (Van Beusechem et al., (1990) J. Exp. Med. 172:729; and Valerio et al., (1989) Gene 84:419). In the present invention, these vectors are called LgXL (ΔMo+ PyF101), wherein X represents the code of a gene yet to be filled in.

Before the results obtained from research into gene transfer into the blood-forming organ of mice can be translated into an eventual use of gene therapy in the clinic, a number of essential questions must be answered by studying a relevant preclinical model. First of all, it has to be demonstrated that efficient gene transfer is also possible to blood-forming stem cells of higher mammals, in particular primates. Moreover, genetic modification coupled with autologous bone marrow transplantation in primates requires complex logistics which cannot be studied in mice. The organization of the blood-forming organs of mice and humans can only be compared to a certain extent and it will be clear that the sizes of the two species, and hence the numbers of cells involved in transplantation, differ considerably.

The experimental animal model that is eminently suitable for preclinical gene therapy studies is the nonhuman primate, in particular the rhesus monkey, partly because the current bone marrow transplantation protocols in the clinic are principally based on data obtained from experiments with bone marrow from the rhesus monkey. Gene therapy procedures using bone marrow cells can be tested in this animal model by taking bone marrow, modifying this genetically by means of recombinant retroviruses and subsequently transplanting it back autologously (i.e. into the same monkey) after the endogenous bone marrow cells have been eradicated by means of irradiation.

To date, such experiments have met with little success with regard to:

a) the hematopoietic regeneration that could be effected with the infected bone marrow, and b) the in vivo stability of the genetic modification.

In the studies published to date, gene transfer was performed either by incubating bone marrow cells with cell-free virus supernatant harvested from virus-producing cells or by a direct exposure of the bone marrow cells to the virus-producing cells. The latter method involves a so-called cocultivation wherein the virus-producing cells are adhered to the bottom of a culture bottle and the bone marrow cells are seeded on top thereof. Following cocultivation, the non-adherent bone marrow cells are subsequently harvested and used as transplants.

In the first reported study (Anderson et al., (1986), Gene transfer and expression in nonhuman primates using retroviral vectors, In Cold Spring Harbor Symposia on Quantitative Biology, Volume LI, eds. Cold Spring Harbor Laboratory, New York, p. 1073; and Kantoff, P. W., A. P. Gillio, J. R. McLachlin, C. Bordignon, et al., (1987) J. Exp. Med. 166:219), in 19 monkeys an autologous transplantation was performed with bone marrow cells infected with different retroviral vectors containing the gene for neomycin resistance (neo$^r$) or dihydrofolate reductase (DHFR), or with a virus in which neo$^r$ and the gene for adenosine deaminase (ADA) are located together, produced by cells that also produce replication-competent virus. Both gene transfer methods described above, i.e., the cocultivation procedure and the infection with virus supernatant that can be harvested from the virus-producing cells were utilized. Using the cocultivation procedure, it was not possible to obtain hematopoietic regeneration after autologous transplantation. As a result, only three out of the 13 monkeys survived this procedure. None of the surviving monkeys showed any signs of genetic modification in vivo. Complete hematopoietic reconstitution could be obtained in the six monkeys that received supernatant-infected bone marrow and in four of these animals the gene could be demonstrated. However, genetic modification remained low and transient. Nor could it be precluded that the observed modification had occurred in long-living T-cells which did not generate from the bone marrow cultured in vitro, but were already present as a contaminant in the infected bone marrow.

In the second study (Bodine et al., (1990) Proc. Natl. Acad. Sci. USA 87:3738) bone marrow from rhesus monkeys was cocultivated with cell lines that produce neo$^r$-containing viruses. In this study, also, only the provirus could be demonstrated in vivo after infection by means of a virus-producing cell line that produces contaminatory helper viruses. In this setting, no long-term studies could be performed because again the bone marrow proved incapable of reconstituting the hematopoietic system.

In conclusion, in the data published so far, the cocultivation method has always been associated with a drastic loss of in vivo regenerating capacity of the bone marrow cells (Anderson et al., (1986), "Gene transfer and expression in nonhuman primates using retroviral vectors", In Cold Spring Harbor Symposia on Quantitative Biology, Volume LI, eds. Cold Spring Harbor Laboratory, New York, p. 1073; Kantoff, P. W., A. P. Gillio, J. R. McLachlin, C. Bordignon, et al., (1987) J. Exp. Med. 166:219; and Bodine et al., (1990) Proc. Natl. Acad. Sci. USA 87:3738), so that a clinical application is precluded.

In addition, none of the studies published to date are sufficiently interpretable as regards genetic modification, since they invariably involved the use of virus preparations in which replication-competent virus was present. Via a so-called "rescue", this may lead to a spread of the recombinant virus genome after the cells have been transplanted, so that it remains unclear whether the modified cells are offspring of infected bone marrow cells. The present invention provides a method for efficient gene transfer into primate hematopoietic stem cells without a significant loss of the in vivo regenerating capacity of the isolated cells.

Relevant Literature

Fibronectin as a single molecule has been reported to bind retroviruses and haemopoietic cells, thereby enhancing the gene transfer efficiency (WO 95/26200).

SUMMARY

The invention provides a method for genetically modifying primate hematopoietic stem cells. The method includes the step of combining isolated primate hematopoietic stem cells with a recombinant retrovirus using means which increase the local concentration of recombinant retrovirus particles in the vicinity of the stem cells over that which is obtained in the absence of such means, so that the chance of infection of the stem cells is enhanced. The recombinant retrovirus contains genetic information to be introduced into the hematopoietic stem cells and has a host range which includes primate hematopoietic stem cells. In some cases it is preferred that the isolated hematopoietic cell population is enriched for hematopoietic stem cells before the hematopoietic stem cells are brought in close physical contact with the recombinant retrovirus. It is preferred that the genome of the recombinant retrovirus is based on a retroviral vector which is derived from a viral MuLV vector. It is furthermore preferred that the recombinant retrovirus has an amphotropic host range. According to the invention the close physical contact provides an efficient genetic modification of the primate hematopoietic stem cells. The close physical contact can be accomplished by various means, which are exemplified in the different embodiments of the invention. Those skilled in the art will be able to use other means to achieve said close physical contact without departing from the present invention.

The term "hematopoietic stem cell" is understood to mean a cell that has the following characteristics: (1) it has the ability to differentiate into any type of cell of the blood cell system, and (2) it has the capacity to multiply itself without losing its characteristics 1 and 2. The term "hematopoietic cell" is understood to mean any cell of the blood cell system, independent of its lineage commitment or maturation state. Thus, "hematopoietic cells" include "hematopoietic stem cells". The term "primates" is understood to mean all primates, including man. Preferably, the gene therapy concerns man. By "close physical contact" is intended a contact which enhances the local concentration of retrovirus particles in the direct vicinity of the target cell beyond that obtained under standard conditions, where "standard conditions" are those where retrovirus particles and target cells are mixed together in a liquid solution at normal gravitation.

In one embodiment of the invention said isolated hematopoietic cells from a primate are, by means of a cocultivation, exposed to cells that produce the recombinant retrovirus. During this cocultivation said isolated hematopoietic cells are in the direct vicinity of said virus-producing cells. In particular, the hematopoietic stem cells from primates are subject to close contact and these cells adhere, in part or possibly preferentially, to said virus-producing cells. During the cocultivation said virus-producing cells continuously produce new recombinant retroviruses that are shed from the cell membrane into the culture medium. After their production, said recombinant retroviruses have a limited life span that depends at least in part on their nature, on the culture temperature and on the composition of the culture medium. Hence, the shorter the distance said recombinant retroviruses have to travel from the site where they were shed into the medium towards the isolated hematopoietic cells from a primate the higher is the chance for a successful genetic modification of said isolated hematopoietic cells of a primate. In this aspect of the invention, therefore, the most efficient genetic modification is obtained for the subset of said isolated hematopoietic cells from a primate that most intimately adhere to said virus-producing cells. For this reason, it is preferred that following cocultivation both non-adherent and adherent cells are harvested.

In another embodiment of the invention the intimate interaction between said virus-producing cells and said hematopoietic stem cells is further improved by forcing these cells together. This can be accomplished by various physical means, including but not restricted to increasing the gravitational force to enhance sedimentation of the hematopoietic stem cells onto the virus-producing cells by centrifugation, centrifuging a mixture of both cell populations onto a solid material, concentrating said mixture on the same physical site by electrodiffusion, forcing by pressure or centrifugation said mixture onto a porous solid material with pores large enough in size to allow passage of the fluid medium but small enough in size to prevent passage of said mixture. In the latter application of the invention, said pressure is either positive pressure applied to said fluid medium or negative pressure applied to said porous solid material or to a space past said porous solid material. Alternatively, said intimate interaction can also be improved by performing the culture in the presence of a compound that binds both the virus-producing cells and the hematopoietic stem cells.

In yet another embodiment of the invention said hematopoietic stem cells are cultured in recombinant retrovirus containing medium in the presence of a compound that binds both the recombinant retrovirus and the hematopoietic stem cell, thus providing the close physical contact between said hematopoietic stem cell and said recombinant retrovirus. Said compound is characterized by its capacity to bind (1) said hematopoietic stem cell, and (2) said recombinant retrovirus and/or said virus-producing cell. It is preferred that said compound besides binding to said recombinant retrovirus or virus-producing cell preferentially, or even exclusively, binds to said hematopoietic stem cell. In this way, said compound selectively increases the genetic modification of said hematopoietic stem cell. Said compound comprises one or more molecules that are selected from or are derived from synthetic or naturally occurring molecules including but not restricted to polymers, antibodies, peptides, cell surface membranes or fragments or components thereof, extracellular matrices or components thereof, intact cells, and complete tissues or components thereof. Said molecules include composite molecules containing parts from molecules of different origin. Preferred compounds in the invention are derived from or are components of the natural hematopoietic microenvironment present in the bone marrow of animals. Said hematopoietic stem cells by nature closely interact with cells and extracellular matrix molecules present in said hematopoietic microenvironment. In addition, said cells produce cytokines that support the maintenance and functioning of said hematopoietic stem cells and said extracellular matrix molecules bind cytokines that support the maintenance and functioning of said hematopoietic stem cells.

The method of the invention is also performed using a different kind of compound that (1) binds to said recombinant retrovirus vector and (2) is immobilized on a solid support material. Said hematopoietic cells of a primate are brought in close contact with said solid support material (and thereby with said bound recombinant retrovirus vector) by any other means exemplified in the various embodiments of the invention (like gravity, electrodiffusion, and fluid flow).

In another embodiment of the invention the close contact between the recombinant retrovirus and the hematopoietic stem cell is accomplished by forcing said recombinant retrovirus towards said hematopoietic stem cell by any of various physical means. These include but are not restricted to increasing the gravitational force by centrifugation to induce settling of the recombinant retrovirus onto the hematopoietic stem cell, causing the recombinant retrovirus to move towards the hematopoietic stem cell by electrodiffusion, and forcing the recombinant retrovirus-containing medium through a bed of hematopoietic cells including said hematopoietic stem cell. In the latter case, said hematopoietic cells are seeded on top of a porous solid material with pores large enough in size to allow passage of the fluid medium but small enough to prevent said cells to pass. In this application of the invention, said force is provided by either normal gravity, increased gravity through centrifugation, positive pressure applied to said medium, or negative pressure applied to said porous solid material or to a space past said porous solid material. In this aspect of the invention it is preferred but not essential that the solid material used binds the recombinant retrovirus.

As is clear from the above, the invention provides means to bring isolated hematopoietic cells including hematopoietic stem cells from a primate in close physical contact with a recombinant retrovirus. This is accomplished either directly, by bringing the recombinant retrovirus itself in close proximity of said isolated hematopoietic cells, or indirectly, by bringing cells that produce the recombinant retrovirus in close proximity of said isolated hematopoietic cells.

According to the invention, it is preferred that the retroviral vector comprises two LTRs (long terminal repeats) derived from a viral MuLV vector and the 5' part of the gag gene of a MuLV. The MuLV sequences are preferably derived from the viral Mo-MuLV vector (Moloney Murine Leukemia Virus), while at least the 3'-LTR is a hybrid LTR which contains the PyF101 enhancer instead of the Mo-MuLV enhancer. To this end, preferably the retroviral vector pLgXL(ΔMo+PyF101) is used, wherein X represents the genetic information to be introduced into the bone marrow cells.

According to the invention, producer cells that can be used include all recombinant retroviral vector producing cell lines with a host range that includes primates. Several examples of producer cell lines that produce retroviral vectors with the LgXL(ΔMo+PyF101) structure useful in the invention have been disclosed in Patent Application WO96/35798. The cells that produce the recombinant retrovirus are preferably recombinant mammalian cells which contain and express the gag pol and env genes of MuLV. The env gene is preferably derived from an amphotropic MuLV. The gag, pol and env genes of MuLV in the recombinant mammalian cells are preferably distributed over at least two different eukaryotic expression vectors. Further, it is preferred that each packaging construct is associated with a selectable marker gene. As recombinant mammalian cells GP+envAM12 cells preferred, it is further preferred that the cells that produce a recombinant retrovirus contain several copies of the retroviral vector.

According to the invention, it is further preferred that the cultivation of hematopoietic stem cells in recombinant retrovirus supernatant or with cells that produce recombinant retrovirus occurs in the presence of serum and at least one hematopoietic growth factor. In some embodiments of the invention, it is further preferred to culture said hematopoietic stem cells for a period of time in the absence of recombinant retrovirus and virus-producing cells before being subjected to genetic modification with recombinant retrovirus or to culture said hematopoietic stem cells for a period of time in the absence of recombinant retrovirus and virus-producing cells after having been subjected to genetic modification with recombinant retrovirus.

The invention further provide cells that produce a recombinant amphotropic retrovirus with a genome based on a retroviral vector, preferably one which is derived from a viral MuLV vector, which contains genetic information that is suitable to be introduced into bone marrow cells of a primate according to the method described herein.

DETAILED DESCRIPTION OF THE INVENTION

The invention provides a method for introducing a gene X into isolated hematopoietic cells including hematopoietic stem cells from a primate, whereby said isolated hematopoietic cells are brought in close contact with a recombinant retrovirus. Preferably, said recombinant retrovirus is an amphotropic retrovirus whose genome is composed of the recombinant retroviral vector pLgXL(ΔMo+PyF101) wherein gene X represents a nucleic acid molecule inserted therein that encodes a ribonucleic acid molecule or a protein which is of importance for gene therapy. The invention is comprised of a number of useful components: a recombinant retroviral vector pLgXL(ΔMo+PyF101), a virus-producing cell line shedding recombinant pLgXL(ΔMo+PyF101) retrovirus, and a method by which isolated hematopoietic cells or purified hematopoietic stem cells of a primate are provided with gene X.

Hematopoietic Cells

Many different standard procedures are known in the art for the collection, storage, processing, and reinfusion of haemopoietic cells from bone marrow, peripheral blood, fetal liver, or umbilical cord blood of primates, as well as for conditioning of the recipient and for post-transplantation supportive care (see, e.g., *Bone Marrow and Stem Cell Processing. A Manual of Current Techniques*, (1992) eds. E. M. Areman, H. J. Deeg, and R. A. Sacher, F. A. Davis Company, Philadelphia, pp. 487; *Marrow Transplantation: Practical and Technical Aspects of Stem Cell Reconstitution*, (1992) eds. R. A. Sacher and J. P. AuBuchon, American Association of Blood Banks, Bethesda, MD, pp. 187). Several methods for stem cell enrichment by CD34+ cell selection are known in the art that use commercially available materials. They have been compared by Wynter et al., *Stem Cells* (1995) 13: 524–532. The MACS Cell Sorting method (Miltenyi Biotec, Germany) gives the best results with respect to purity and recovery, and is thus preferred.

True in vitro tests for haemopoietic stem cells do not exist, but phenotypic analysis is usually performed as an indicator of the quality of both the isolated material and the graft after gene transfer (Knaän-Shanzer et al., *Gene Therapy* (1996) 3:323–333). In the experiments with rhesus monkeys described in the examples this was not done, because not all essential antibodies for this analysis react with rhesus monkey cells. There is no special treatment of the cells prior to cultivation with retrovirus particles.

Recombinant Retroviral Vector pLgXL(ΔMo+PyF101)

The recombinant retroviral vector includes DNA elements originating from a MuLV which are necessary in cis for the packaging, reverse transcription and integration of the retroviral genome; these include two so-called Long Terminal Repeats (LTR) and the so-called packaging sequences. In the LTR a modification has been provided by replacing the enhancer originating from MuLV with the enhancer of the polyoma virus strain PyF101 (Linney et al., (1984) *Nature* 308:470). In the plasmid construct, it is not necessary that this modification is present in both LTRs; only the 3' LTR must be provided with the modification since that portion of the LTR ends up in both LTRs after a viral infection (Van Beusechem et al., (1990) *J. Exp. Med.* 172:729; and Valerio et al., (1989) *Gene* 84:419), and the 5' part of the MuLV gag-encoding sequences such as present in the vector N2 (Armentano, D., S. F. Yu, P. W. Kantoff, T. Von Ruden, W. F. Anderson and E. Gilboa, (1987), Effect of internal viral sequences on the utility of retroviral vectors, *J. Virol.* 61:1647), so as to effect a higher viral titer. Optionally, the ATG initiation codon of gag can be mutated by means of site-directed mutagenesis, so that it is no longer a translation start site. The only absolute requirements for the vector are (i) the inclusion of DNA elements necessary in cis for the packaging, reverse transcription, and integration of the retroviral genome, and (ii) that the gene X be placed within a proper transcription unit, wherein it is preferred that this transcription unit is a natural viral transcription unit (no internal promoter). The pLgXL(ΔMo+PyF101) vector meets these requirements and includes some further improvements, as exemplified above.

The retroviral vector is included in a plasmid construct having plasmid sequences necessary for propagation of the vector in *E. Coli* bacteria such as for instance pBR322 (Bolivar et al., (1977) *Gene* 2:95) or a vector from the pUC series (Vieira and Messing, (1982) *Gene* 19:259); on these, both an origin of replication and a selectable gene (for instance for ampicillin of tetracycline resistance) are present, together with gene X. The term "gene" is to be understood to mean a nucleic acid molecule encoding a ribonucleic acid molecule or protein. It includes naturally occurring nucleic acid molecules and synthetic derivatives thereof. Useful genes that encode a ribonucleic acid molecule or a protein which is of importance for gene therapy include, but are not restricted to, all genes associated with hereditary disorders wherein a therapeutic effect can be achieved by introducing an intact version of the gene into somatic cells. Most of them are documented in:

McKusick, *Mendelian Inheritance in Man, Catalogs of Autosomal Dominant, Autosomal Recessive, and X-Linked Phenotypes*. Eighth edition. John Hopkins University Press (1988), and Stanbury et al., *The Metabolic Basis of Inherited Disease*. Fifth edition. McGraw-Hill (1983).

Examples of gene X include:
  genes associated with diseases of the carbohydrate metabolism such as for: fructose-1-phosphate aldolase; fructose-1,6-diphosphatase; glucose-6-phosphatase; lysosomal α-1,4-glucosidase; amylo-1,6-glucosidase; amylo-(1,4:1,6)-transglucosidase; muscular phosphorylase; liver phosphorylase; muscular phosphofructokinase; phosphorylase-b-kinase; galactose-1-phosphate uridyl transferase; galactokinase; all enzymes of the pyruvate dehydrogenase complex; pyruvate carboxylase; 2-oxoglutarate glyoxylate carboligase; and D-glycerate dehydrogenase;

genes associated with diseases of the amino acid metabolism such as for: phenylalanine hydroxylase; dihydrobiopterin synthetase; tyrosine aminotransferase; tyrosinase; histidase; fumarylacetoacetase; glutathione synthetase; γ-glutamylcysteine synthetase; orinithine-δ-aminotransferase; carbamoylphosphate synthetase; ornithine carbamyltransferase; argininosuccinate synthetase; argininosuccinate lyase; arginase; L-lysine dehydrogenase; L-lysine ketoglutarate reductase; valine transaminase; leucine isoleucine transaminase; "branched chain" 2-keto acid decarboxylase; isovaleryl CoA dehydrogenase; acyl-CoA dehydrogenase; 3-hydroxy-3-methylglutaryl CoA lyase; acetoacetyl CoA 3-ketothiolase; propionyl CoA carboxylase; methylmalonyl CoA mutase; ATP:cobalamine adenosyltransferase; dihydrofolate reductase; methylene tetrahydrofolate reductase; cystathionine β-synthase; sarcosine dehydrogenase complex; proteins belonging to the glycine cleavage system; β-alanine transaminase; serum carnosinase; and cerebral homocarnosinase;

genes associated with diseases of fat and fatty acid metabolism such as for: lipoprotein lipase; apolipoprotein C-II; apolipoprotein E; other apolipoproteins; lecithin cholesterol acyltransferase; LDL receptor; liver sterol hydroxylase; and "Phytanic acid" α-hydroxylase;

genes associated with lysosomal defects such as for: lysosomal α-L-iduronidase; lysosomal iduronate sulfatase; lysosomal heparin N-sulfatase; lysosomal N-acetyl-α-D-sulfatase; lysosomal acetyl CoA:α-glucosaminide N-acetyltransferase; lysosomal N-acetyl-α-D-glucosaminide 6-sulphatase; lysosomal galactosamine 6-sulphate sulfatase; lysosomal β-galactosidase; lysosomal arylsulfatase B; lysosomal β-glucuronidase; N-acetylglucosaminylphosphotransferase; lysosomal α-D-mannosidase; lysosomal α-neuraminidase; lysosomal aspartylglycosaminidase; lysosomal α-L-fucosidase; lysosomal acid lipase; lysosomal acid ceramidase; lysosomal sphingomyelinase; lysosomal glucocerebrosidase; lysosomal galactosylceramidase; lysosomal arylsulfatase A; α-galactosidase A; lysosomal acid β-galactosidase; and α-chain of the lysosomal hexosaminidase A;

genes associated with diseases of the steroid metabolism such as for: 21-hydroxylase; 11β-hydroxylase; androgen receptor; steroid 5α-reductase; steroid sulfatase;

genes associated with diseases of the purine and pyrimidine metabolism such as for: phosphoribosylpyrophosphate synthetase; hypoxanthine guanine phosphoribosyltransferase; adenine phosphoribosyltransferase; adenosine deaminase; purine nucleoside phosphorylase; AMP deaminase; xanthine oxidase; orotate phosphoribosyltransferase; orotidine 5'-phosphate decarboxylase; and DNA repair enzymes;

genes associated with diseases of the polphyrin and heme metabolism such as for: uroporphyrinogene III cosynthase; ferrochelatase; porphobilinogen deaminase; coproporphyrinogen oxidase; proporphyrinogene oxidase; uroporphyrinogene III synthase; uroporphyrinogene decarboxylase; bilirubin UDP-glucuronyltransferase; and catalase.

genes associated with diseases of the connective tissue, muscles and bone such as for: lysyl hydroxylase;

procollagen peptidase; α1-antitrypsin; dystrophin; alkaline phosphatase; and guanosine nucleotide regulatory protein of the adenyl cyclase complex;

genes associated with diseases of the blood and blood-forming organs such as for: blood coagulation factor V; blood coagulation factor VII; blood coagulation factor VII; blood coagulation factor IX; blood coagulation factor X; blood coagulation factor XII; blood coagulation factor XIII; all other blood coagulation factors; all genes associated with osteopetrosis such as for: "carbonic anhydrase II"; thrombocytes membrane glycoprotein Ib; thrombocytes membrane glycoprotein IIb–IIIa; spectrin; pyruvate kinase; glucose-6-phosphate dehydrogenase; NADH cytochrome $b_5$ reductase; β-globin; and α-globin;

genes associated with diseases of transport systems such as for: lactase; sucrase-α-dextrinase; 25-hydroxyvitamin $D_3$- 1 -hydroxylase; and cystic fibrosis transport regulator;

genes associated with congenital immunodeficiencies such as for: the proteins of the complement system including B, Clq, Clr, C2, C3, C4, C5, C7, C8 and C10; the inhibitor of Cl, a component of the complement system; the inactivator of C3b, a component of the complement system;

genes for X-linked immunodeficiencies such as for: one of the enzymes of the NADPH oxidase complex; myeloperoxidase; and the syndrome of Wiscott Aldrich and Ataxia Telangiectasia;

genes coding for hormones as well as the genes coding for their receptors such as for instance for growth hormone.

Gene X also includes genes which (to date) have not been associated with a hereditary defect but with which gene therapy can be practiced in some manner. These include: the gene for tyrosine hydroxylase, drug resistance genes such as for instance: the P-glycoprotein P170 (the so-called multi drug resistance gene mdr1); mdr 3; dihydrofolate reductase (DHFR) and methotrexate resistant isotypes thereof; metallothionine; aldehyde dehydrogenase (ALDH); and glutathione transferase; genes coding for all cytokines including for instance all interleukins and all interferons; genes coding for all growth factors; genes coding for all growth factor receptors; genes coding for all transplantation antigens such as for instance the major and minor histocompatibility antigens; genes capable of affording resistance against infectious organisms, such as for instance TAR decoys (Sullenger et al., (1990) *Cell* 63:601), antisense ribonucleic acid molecules, ribozymes, and intracellular antibodies; genes of infectious organisms which can be used for vaccination purposes such as for instance the envelope gene of HIV; and genes which can be used for negative selection such as for instance the thymidine kinase gene of the Herpes simplex virus against which selection can be effected with substrates such as for instance gancyclovir or acyclovir (Borelli et al., (1988), *Proc. Natl. Acad. Sci. USA* 85:7572; and Mansour et al., (1988) *Nature* 336:348).

The Virus-producing Cells

In order to obtain a stable, selectable virus-producing cell line which produces the amphotropic recombinant retrovirus, pLgXL(ΔMo+PyF101) is introduced into an amphotropic packaging cell line that is selected for the presence of the DNA sequences which are of importance for the production of the viral proteins. One example of such a cell line is GP+envAm12 (Markowitz et al., (1988) *Virology* 167:400). It has been demonstrated, on the other hand, that ψCRIP is not selectable and is unstable with respect to virus production (Danos and Mulligan, (1988) *Proc. Natl. Acad. Sci. USA* 85:6460).

The selectable packaging cell line is based on mammalian cells and produces all viral proteins that are coded by the gag, pol and env genes of MuLV. The env gene must originate from a virus with a tropism including primates, and is preferably derived from an amphotropic MuLV. In order to obtain expression of the aforementioned viral genes, they, while cloned in a eukaryotic expression vector, must be under control of a promoter active in the host, preferably a RNA polymerase II promoter, and be followed by a polyadenylation signal. On these so-called packaging constructs, all three viral genes may be present simultaneously as for instance described by Miller (Miller and Buttimore (1986) *Mol. Cell. Biol.* 6:2895), but the genes may also occur separately on two expression vectors as described by Markowitz (Markowitz et al., (1988) *Virology* 167:400). This last is to be preferred because it reduces the chances of recombination events leading to helper virus formation.

As stated, a useful characteristic of the packaging cell line to be used for this invention is the possibility it provides means of selecting for the presence of the above-mentioned packaging constructs. This can be achieved by effecting a physical association of the packaging constructs with a selectable marker gene. This association can be achieved by combining them in one vector (as done with pGag-PolGPT in reference (Markowitz et al., (1988) *J. Virol.* 62:1120) or by means of a so-called cotransfection (review in for instance (Pellicer et al., (1980) *Science* 209:1414). The successfully transfected cells can then be isolated by selecting for the marker gene. Since the cotransfected DNA fragments mostly end up ligated to each other at one place in the genome of the transfected cell (Pellicer et al., (1980) *Science* 209:1414), the thus selected cells will mostly contain the packaging construct as well. In view of the fact that ψCRIP cells have been made in this way and, nevertheless, are not selectable, the last procedure is not always successful and the construction of vectors with the marker gene cloned into it is to be preferred.

As a marker gene, genes coding for a large number of different proteins can be used. Widely used and preferred marker genes are: the neomycin resistance gene (Southern and Berg, (1982) *J. Mol. Appl. Genet.* 1:327), the hygromycin resistance gene (Blochlinger and Diggelman (1984) *Mol. Cell. Biol.* 4:2929), the *E. coli* xanthine-guanine phosphoribosyl transferase (gpt) gene (Mulligan and Berg (1980) *Science* 209:1422), the histidinol gene (Hartman and Mulligan (1988) *Proc. Natl. Acad. Sci. USA* 85:8047), the herpes simplex virus thymidine kinase gene (Colbère-Garapin et al., (1979) *Proc. Natl. Acad. Sci. USA* 76:3755) and the methotrexate resistant isotype of dihydrofolate reductase (Simonsen and Levinson (1983) *Proc. Natl. Acad. Sci. USA* 80:2494). These genes must also be under control of a suitable promoter, in particular a RNA polymerase II promoter, and be followed by a polyadenylation signal.

The introduction of pLgXL(ΔMo+PyF101) can be effected by means of various physical techniques such as calcium-phosphate precipitation, electroporation or lipofection (Graham and Van der Eb, (1973) *Nucl. Acids Res.* 15:13 11; Potter et al., (1984) *Proc. Natl. Acad. Sci. USA* 81:7161; Felgner and Ringold (1989) *Nature* 337:387; Felgner et al., (1987) *Proc. Natl. Acad.*

*Sci. USA* 84:7413). If the packaging cells cannot be selected for the presence of pLgXL(ΔMo+PyF101), use is made of a selectable marker such as for instance an expression vector of the neomycin resistance gene which is transfected together with pLgXL(ΔMo+PyF101). The successfully transfected cells are then be selected by selecting for the marker gene. Since the DNA fragments mostly end up ligated to each other in one place in the genome of the transfected cell, the thus selected cells will mostly contain the retroviral vector as well.

A preferred procedure is the introduction of pLgXL (ΔMo+PyF101) via an infection. Since viruses are not capable of infecting packaging cells of the same tropism, use must be made of a version of the recombinant retrovirus with a different tropism which is obtained by introducing the DNA initially via a physical technique into packaging cells with said different tropism. For example, ecotropic virus produced by ecotropic packaging cells transfected with a pLgXL(ΔMo+PyF101) construct can be used to infect amphotropic packaging cells. The infected cells are cloned and then tested for their ability to produce virus.

Further, it is possible to obtain cell lines producing a higher titer of the virus by introducing several copies of the retroviral vector into the packaging cells using the so-called "ping-pong" method (Bestwick et al., (1988) *Proc. Natl. Acad. Sci. USA* 85:5404; and Kozak and Kabat (1990) *J. Virol.* 64:3500). In this method, an ecotropic virus-producing cell line is cocultivated with amphotropic packaging cells, which can give rise to repeated infections. In order to enable the amphotropic cells to be cloned back after this cocultivation, they must be selectable with selective media in which the ecotropic packaging cells do not survive. By plating the cells in such medium, the proper virus-producing clones can be isolated and subsequently analyzed for their capacity to produce the recombinant virus.

Method by which Hematopoietic Cells of a Primate can be provided with Gene X, in such a Manner that the Regeneration Capacity of the Hematopoietic Cells is Maintained and Autologous Transplantation of the Hematopoietic Cells gives rise to a Genetically Modified Hematopoietic System The above-mentioned recombinant retroviral vectors are used for the efficient introduction of gene X into hematopoietic cells of primates by bringing said hematopoietic cells in close physical contact with said recombinant retroviral vectors. A key aspect of the invention is the realization that the efficiency of gene transfer is in part dependent on the chance for a recombinant retroviral vector particle to associate with its receptor on the surface of a hematopoietic target cell. Thus, important factors determining the efficiency of recombinant retroviral vector-mediated gene transfer into hematopoietic cells of primates include (1) the concentration of recombinant retroviral vector particles at the site of the hematopoietic target cell, (2) the density and affinity of receptors for the recombinant retroviral vector on the surface of the target cell, (3) the stability of the recombinant retroviral vector particle, and (4) the stability of the hematopoietic target cell. Information relative to these factors is as follows.

To optimize the concentration of recombinant retroviral vector particles at the site of the target cell, one can increase the total concentration of recombinant retroviral vector particles in the culture medium, by improving the virus-producing cell line or the virus production and harvest procedure. This invention provides an additional method to increase the concentration of recombinant retroviral vector particles at the site of the hematopoietic target cell, i.e., by establishing a close physical contact between the recombinant retroviral vector and said target cell according to one of several means which are exemplified in detail below.

For the scope of the invention, the density and affinity of receptors for the recombinant retroviral vector on the surface of a certain target cell are regarded as naturally constant factors. Although perhaps receptor expression or integrity on target cells could be influenced, e.g. by changing the culture conditions, this is not part of the invention. It is realized, however, that receptor densities may intrinsically differ between different cell types significantly. It is furthermore realized that especially for cell types with very few functional receptors for the recombinant retroviral vector, which may include the hematopoietic stem cell, it is important to enhance the chance for a virus-to-cell encounter. This will be even more important when a target cell with few functional receptors is part of a cell mixture containing other cell types having higher functional receptor densities.

In general, the half-life of infectious recombinant retroviral vector particles under standard culture conditions is low (3–9 hours; e.g., Kotani et al., *Hum. Gene Ther.* 5(1994)19–28; Forestell, et al., *Gene Ther.* 2(1995) 723–730). This half-life can be increased by lowering the culture temperature to 32° C. (Kotani et al., *Hum. Gene Ther.* 5(1994) 19–28). Methods to increase the stability of the recombinant retroviral vector particles are not part of the invention. It is realized, however, that the invention providing an increased chance for a virus-to-cell encounter is of particular importance for retroviral vectors with a short half-life.

It is of critical importance that a method to transfer a gene X into a certain target cell allows said target cell to retain all of its characteristics. Especially in the case of hematopoietic stem cells of primates this has previously been difficult, if not impossible, to achieve. Gene transfer procedures tested on bone marrow grafts of primates led to a dramatic loss of the in vivo regenerating capacity of the grafts (see above). The present invention provides a method for efficient transfer of gene X into hematopoietic stem cells of primates that does not significantly affect the in vivo regenerating capacity of the manipulated graft.

Numerous different procedures for harvest, processing, storage, shipping, etc. of human haemopoietic cells are in use and known to those of skill in the art. Various means of bringing together of the recombinant retrovirus particles and hematopoietic target cells include the following:

General Procedure for Recombinant Retroviral-vector Mediated Gene Transfer into Hematopoietic Cells of Primates:

The hematopoietic cells of a primate are suspended in a suitable culture medium for hematopoietic cells containing recombinant retrovirus vector particles. Said hematopoietic cells are either total mononuclear cells or are cell populations that are enriched for stem cells according to various methods known in the art, including but not restricted to, density separation (Percoll, BSA) and positive selection for CD34+cells (FACS sorting, Dynabeads immunoselection, Miltenyi MACS selection, AIS CELLector flask selection, or CellPro CEPRATE selection) or depletion of cells carrying mature cell type cell surface markers. Many different suitable culture media are commercially available. They include, but are not restricted to DMEM, IMDM, and α-MEM, with 5–30% serum and often further supplemented with, e.g., BSA, one or more antibiotics. L-glutamine, 2-mercaptoethanol, hydrocortisone, and hematopoietic growth factors. Recombinant retrovirus vector particles are harvested into this medium by incubating virus-producing cells in this medium. To enhance gene transfer, usually compounds such as polybrene, protamine sulphate, or protamine HCl are added. Usually, the cultures are maintained for 2–4 days and the recombinant retrovirus vector containing medium is refreshed daily. Optionally, the hematopoietic cells are precultured in medium with growth factors but without recombinant retrovirus vector particles for up to 2 days, before adding the recombinant retrovirus vector containing medium.

For successful gene transfer it is essential that the target cells undergo replication in culture (without differentiation). Most harvested haemopoietic stem cells are resting cells. Therefore, a stimulus to enter cell cycle during culture is needed. This can be accomplished by adding recombinant haemopoietic growth factors (HGF), including different combinations of HGF such as interleukin-3, interleukin-6, and steel factor (SCF). In cultures with stromal cell support, or other cells which produce the necessary HGF, such as a retrovirus producing cell line, HGF addition is not needed.

The method of the invention is performed according to one of the following procedures, either indirectly, by bringing hematopoietic cells of a primate in close physical contact with virus-producing cells, or directly, by bringing hematopoietic cells of a primate in close physical contact with recombinant retroviral vector particles.

The following are examples of indirect methods which are used.

i) Cocultivation of Hematopoietic Cells of a Primate with Virus-producing Cells. Said virus-producing cells and the hematopoietic cells from a primate are mixed at the initiation of the coculture, or a monolayer of adherent virus-producing cells is established before adding said hematopoietic cells from a primate. Said virus-producing cells may have been damaged prior to initiation of the coculture by, e.g., a lethal dose of irradiation, but can be used so long as they continue to shed recombinant retroviral vector particles into the medium. Said virus-producing cells have the capacity to bind said hematopoietic cells to their surface. Virus-producing cells based on the commonly used packaging cells derived from mouse fibroblasts have this capacity. Due to the intimate interaction between said virus-producing cell and said hematopoietic cell the recombinant retroviral vectors produced by said virus-producing cell only have to travel a very short distance to reach said hematopoietic cell. It may even occur that a recombinant retroviral vector fuses with the membrane of the hematopoietic cell while being shed from the membrane of the virus-producing cell. The invention thus provides a transduction method that minimizes the time during which the recombinant retroviral vector is exposed to de-stabilizing components of the environment. The most efficient genetic modification is obtained for the subset of hematopoietic cells of a primate that most intimately adhere to the virus-producing cells. It is preferred that said virus-producing cells preferentially, or even exclusively, bind hematopoietic stem cells. In this way, the genetic modification of said hematopoietic stem cells is selectively increased. In this embodiment of the invention, it is preferred that the cocultivation takes place for three to four days in the presence of serum and one or more hematopoietic growth factors such as for instance interleukin 3 (IL-3). Following cocultivation, both the non-adherent and the adherent cells are harvested from the culture (the last-mentioned cells can be obtained by, e.g., trypsinization) and used as the transplant.

ii). Cocultivation of Hematopoietic Cells of a Primate with Virus-producing Cells at Increased Gravitational Force. This embodiment of the invention provides a further improvement of and includes the advantages of the procedure described under (i). Apart from the increased gravitational force, the procedure is performed as described under (i). By increasing the gravitational force two effects are being accomplished, i.e., (1) the intimate interaction between the virus-producing cells and the hematopoietic cells from a primate is further enhanced, and (2) recombinant retrovirus vector particles that have been shed into the culture medium are prevented from traveling away from the hematopoietic cells, thus increasing the local concentration of said particles. Said increased gravitational force is achieved by performing the cocultivation while spinning the container with the culture around an axis of rotation. Said axis can intersect said container or be located outside of said container. Useful centrifuges to spin the cultures according to the invention are known in the art. The gravitational force is maximized, but should not exceed the maximal gravitational force that allows functional survival of the virus-producing cells, the recombinant retroviral vector particles and the hematopoietic cells from a primate. Usually, said gravitational force will not exceed 2500 g As a result of the further increased gene transfer efficiency obtained with this embodiment of the invention, the coculture duration can be significantly shortened. Usually, this procedure will not be performed for more than eight consecutive hours.

iii). Cocultivation of Hematopoietic Cells of a Primate with Virus-producing Cells with Increased Inter-cellular Contact Accomplished by Electrodiffusion. This embodiment of the invention provides an alternative improvement of and includes the advantages of the procedure described under (i). Apart from the electrodiffusion, the procedure is performed as described under (i). Because the hematopoietic cells of a primate, the virus-producing cells, and the recombinant retroviral vector particle are all negatively charged they can be forced to move towards a positive electrode. By performing the cocultivation procedure in an electrophoresis unit said negatively charged cells and vectors are concentrated. This way, two objectives are accomplished, i.e., (1) the intimate interaction between the virus-producing cells and the hematopoietic cells from a primate is further enhanced, and (2) the recombinant retrovirus vector particles that have been shed into the culture medium are prevented from traveling away from the hematopoietic cells, thus increasing the local concentration of said particles. Electrophoresis units useful for this aspect of the invention are known in the art. Said electrophoresis unit preferably contains two chambers separated by a semi-permeable membrane, with pore sizes that do not permit passage of said cells and vectors. In such a two-chamber electrophoresis unit said cocultivation is performed in the chamber containing the negative electrode. The voltage applied between the electrodes is maximized, but kept below a value that causes significant damage to said hematopoietic cells of a primate, said virus-producing cells, and said recombinant retroviral vector particles. To further reduce said damage, said voltage may be applied periodically. Also in this embodiment of the invention, said virus-producing cells and said hematopoietic cells from a primate are mixed at the initiation of the coculture, or a monolayer of adherent virus-producing cells is established on the surface of said semi-permeable membrane before adding said hematopoietic cells from a primate.

iv). Cocultivation of Hematopoietic Cells of a Primate with Virus-producing Cells with Increased Inter-cellular Contact Accomplished by Fluid Flow. This embodiment of the invention provides another alternative improvement of an includes the advantages of the procedure described under (i). Apart from the fluid flow, the procedure is performed as described under (i). Said fluid flow is brought about by forcing the culture medium through a porous solid material with pores large enough in size to allow passage of said culture medium but small enough in size to prevent passage of said hematopoietic cells of a primate and said virus-producing cells. Said pores may or may not allow passage of the recombinant retroviral vectors. The force driving said fluid flow is exercised by normal or increased gravitational force or by positive pressure applied to said culture medium or by negative pressure applied to said porous solid material or to a space past said porous solid material. Said increased gravitational force is achieved by performing the cocultivation while spinning the container with the culture around an axis of rotation. Said axis can intersect said container or be located outside of said container. Said pressure is established using a pump device. Pump and centrifuge devices useful in this aspect of the invention are known in the art. The rate of the fluid flow depends in part on the size of the pores in the solid material: if said pores allow passage of the recombinant retroviral vectors the rate is at a value that at least compensates for random diffusion of the recombinant retroviral vector; if said pores do not allow passage of the recombinant retroviral vector the rate is maximized; but in no case may said rate exceed the maximal rate that allows functional survival of the virus-producing cells, the recombinant retroviral vector particles and the hematopoietic cells from a primate. Also in this embodiment of the invention, said virus-producing cells and said hematopoietic cells from a primate are mixed at the initiation of the coculture, or a monolayer of adherent virus-producing cells is established on the surface of said porous solid material before adding said hematopoietic cells from a primate.

v). Cocultivation of Hematopoietic Cells of a Primate with Virus-producing Cells in the Presence of a Compound that Binds Both said Hematopoietic Cells of a Primate and said Virus-producing Cells. This embodiment of the invention provides another alternative improvement of and includes the advantages of the procedure described under (i). Apart from said compound, the procedure is performed as described under (i). Said compound has at least one binding site for said hematopoietic cell of a primate and at least one binding site for said virus-producing cell. The nature of said binding sites may be different or the same. Said compound is a soluble molecule or a solid support material or comprises several soluble molecules bound directly or indirectly to each other or comprises one or more soluble molecules bound to the same solid support material. Said indirect binding may be via a homogeneous or heterogeneous complex of molecules, via cell surface membranes or fragments or components thereof, via intact cells, or even via a complex mixture of different cells. Said mixture of cells may be artificially composed or be derived from naturally occurring cell mixtures or tissues. Thus, it is to be understood that said compound, may, e.g., comprise a complete naturally occurring tissue. Another nonlimiting example of a compound in this embodiment of the invention is a tissue culture plastic with a coating that binds to said hematopoietic cells of a primate and said virus-producing cells. In this embodiment of the invention it is preferred that said binding site for a hematopoietic cell of a primate has a binding preference for hematopoietic stem cells over other types of hematopoietic cells.

Preferred compounds in this aspect of the invention are derived from or are components of the natural hematopoietic microenvironment present in the bone marrow of animals. Said hematopoietic stem cells by nature closely interact with cells and extracellular matrix molecules present in said hematopoietic microenvironment. In addition, said cells produce cytokines that support the maintenance and functioning of said hematopoietic stem cells and said extracellular matrix molecules bind cytokines that support the maintenance and functioning of said hematopoietic stem cells. We are using a cultured stroma cell population. This is a complex mixture of cells, extracellular matrix molecules and the cytokines produced by the cultured cells. The stroma culture significantly enhances the recovery of a phenotypically defined candidate human hematopoietic stem cell population (approx. 10-fold). Components of the extracellular matrix include collagens, proteoglycans, fibronectin, laminin, elastin, glycosaminoglycans, thrombospondin, and chondronectin.

Further preferred compounds in this aspect of the invention comprise parts that are derived from antibodies or from peptides with a defined binding capacity. Said peptides may be naturally occurring or artificially synthesized or derived from a combinatorial peptide library, including but not restricted to a library made by phage display. Preferred peptides in this aspect of the invention are derived from proteins that are involved in natural inter-cellular adhesion and/or signal transduction processes, where it is more preferred that said natural processes involve at least one cell type of the hematopoietic system.

A typical nonlimiting example of a compound according to this aspect of the invention is a tissue culture plate coated with a mixture of antibodies directed against molecules on the surface of the virus-producing cell (e.g., retroviral envelope molecules) and molecules on the surface of the hematopoietic cell (e.g., the CD34 molecule present on the membrane of primitive hematopoietic cells), or with bispecific antibodies directed against both cell populations, or with a mixture of synthetic peptides directed against both cell populations (including, e.g., peptides derived from cytokines known to act on said hematopoietic cells by binding to a specific receptor molecule).

The following are examples of direct methods which are used for bringing hematopoietic primate cells into close physical contact with recombinant retroviral vector particles. These embodiments of the invention make use of cell-free recombinant retroviral vector preparations derived from the culture medium of virus-producing cells that is harvested according to standard procedures known in the art. These procedures may include purification, concentration, and the like.

vi). Sedimentation of Recombinant Retrovirus Vectors onto Hematopoietic Cells of a Primate at Increased Gravitational Force. Said increased gravitational force is achieved by incubating said hematopoietic cells in recombinant retroviral vector containing medium while spinning the container with the culture around an axis of rotation according to the procedure described in embodiment (ii). Said gravitational force should at least be higher than the minimal force needed to overcome the random diffusion of the recombinant retroviral vector and should not exceed the maximal gravitational force that allows functional survival of the recombinant retroviral vector and the hematopoietic cells from a primate, where it is preferred that the gravitational force is maximized. Usually, said gravitational force will not exceed 2500 g. the centrifugation time depends on the centrifugation speed and on the height of the column of culture medium above the hematopoietic cells, but typically does not exceed two recombinant retroviral vector half-lives. Optionally, the procedure may be repeated several times with fresh recombinant retroviral vector containing medium.

vii). Electrodiffusion of Recombinant Retroviral Vectors Towards Hematopoietic Cells of a Primate. By performing the cultivation of said hematopoietic cells of a primate in recombinant retroviral vector containing medium in an electrophoresis unit said hematopoietic cells of a primate and recombinant retroviral vector particles that are both negatively charged are forced to move in the same direction towards the positive electrode and thus are concentrated. Electrophoresis units useful for this aspect of the invention are known in the art. Said electrophoresis unit preferably contains two chambers separated by a semi-permeable membrane, with pore sizes that do not permit passage of said hematopoietic cells of a primate and said recombinant retroviral vectors. In such a two-chamber electrophoresis unit the cultivation is performed in the chamber containing the negative electrode. The voltage applied between the electrodes is maximized, but kept below a value that causes significant damage to said hematopoietic cells of a primate and said recombinant retroviral vector particles. To further reduce said damage, said voltage may be applied periodically. Also in this embodiment of the invention, the procedure is typically not performed for longer than two recombinant retroviral vector half-lives and may be repeated several times with fresh recombinant retroviral vector containing medium.

viii). Forcing Recombinant Retroviral Vector Particles Towards Hematopoietic Cells of a Primate by Fluid Flow. Said fluid flow is brought about by forcing the culture medium containing the recombinant retroviral vectors through a porous solid material with pores large enough in size to allow passage of said culture medium but small enough in size to prevent passage of said hematopoietic cells of a primate. Said pores may or may not allow passage of the recombinant retroviral vectors. The force driving said fluid flow is exercised as exemplified above under iv). The rate of the fluid flow may range from the value that compensates for random diffusion of the recombinant retroviral vector to the maximal rate that allows functional survival of the recombinant retroviral vector particles and the hematopoietic cells from a primate. The time during which the fluid flow is maintained typically does not exceed two recombinant retroviral vector half-lives. Optionally, the procedure may be repeated several times with fresh recombinant retroviral vector containing culture medium.

ix). Culture of Hematopoietic Cells of a Primate in Recombinant Retroviral Vector Containing Medium in the Presence of a Compound that Binds Both said Hematopoietic Cells of a Primate and said Recombinant Retroviral Vector. Said compound has at least one binding site for said hematopoietic cell of a primate and at least one binding site for said recombinant retroviral vector. The nature of said binding sites may be different or the same. Said compound is selected from or derived from the same molecules and materials characterized above under (v).

Also in this embodiment of the invention it is preferred that said binding site for a hematopoietic cell of a primate has a binding preference for hematopoietic stem cells over other types of hematopoietic cells.

Also in this aspect of the invention, preferred compounds are derived from or are components of the natural hematopoietic microenvironment present in the bone marrow of animals. Further preferred compounds in this aspect of the invention comprise parts that are derived from antibodies or from peptides with a defined binding capacity as characterized above under (v). A typical nonlimiting example of a compound according to this aspect of the invention is a tissue culture plate coated with a mixture of antibodies directed against the envelope molecule on the surface of the recombinant retroviral vector and molecules on the surface of the hematopoietic cell, or with bispecific antibodies directed against said vector and cell, or with a mixture of synthetic peptides directed against said vector (e.g., peptides derived from the receptor for the retrovirus envelope molecule) and said cell.

x). Binding the Recombinant Retroviral Vector to a Compound that is Immobilized on a Solid Support Material that is Brought in Close Contact with the Hematopoietic Cells of a Primate by Anyone of the Means Exemplified in Embodiments VI–VIII or Similar Procedures. Compounds useful in this aspect of the invention have at least one binding site for said recombinant retroviral vector while being immobilized to said solid support material by any physical or chemical means. Said solid support materials include but are not restricted to plastics, silicates, metals, and the like. Additional examples of solid support materials include agarose, sephrose, sephadex, cellulose (acetate), DEAE-cellulose, polyacrylamide, polystyrene, Tosylactivated polystyrene, glass, gelatin, dextran, polyethylene, polyurethane, polyester. A nonlimiting example of this embodiment of the invention is the use of a plastic tissue culture dish (the solid support material) coated by standard procedures known in the art with antibodies directed against the retrovirus envelope protein (the compound). Additional examples of solid support materials, in terms of physical structure: single or multi-layer tissue culture dish or flask, semi-permeable membrane, porous or non-porous beads including immunomagnetic beads, and (hollow) semi-permeable or non-permeable fibers. Methods of coating and coupling the compound to the solid support materials include the following.

For polystyrene a simple adsorption procedure can be followed. Protein dissolved in PBS is incubated for several hours at room temperature with the solid support material. Subsequently, the coated solid support material is washed once or several times in PBS or in PBS with 0.1% (w/v) irrelevant protein such as, e.g., albumin.

For other materials, covalent binding is preferred for efficient coating. Many coupling procedures and useful materials are known in the art and are commercially available, e.g., CNBr-activated sepharose (manufactured by Pharmacia) or agarose or dextran can be used to couple ligands containing amino groups by incubating them with ligand dissolved in a bicarbonate or borate buffer at high pH (preferably in the range of 8–10) with a high salt content (preferably approximately 0.5M NaCl) for 2 hours at room temperature or for 10–16 hours at 4° C. Subsequently, excess ligand is washed away with coupling buffer, any remaining active groups are blocked with, e.g., 01. M Tris-HC 1 buffer pH 8.0 for 2 hours at room temperature or for 10–16 hours at 4° C., and ionically bound free ligand is washed away by alternatively washing with high and low pH buffer solutions such as, e.g., Tris-HC1 buffer pH 8.0 with 0.5M NaCl and 0.1M acetate buffer pH 4.0 with 0.5M NaCl. Another example is polystyrene activated by p-toluenesulfonyl chloride treatment (such as the Tosylactivated Dynabeads M-450 manufactured by Dynal). Any protein or glycoprotein can be chemically coupled to this material by incubating the solid support material with the ligand dissolved in a high pH buffer such as 0.5M borate buffer pH 9.5 for 24 hours at room temperature. Unbound ligand is removed by several washes with PBS with 0.1% irrelevant protein (such as albumin). Many alternative coupling procedures and commercially available activated soluble support materials useful in the invention are known in the art (see, e.g., *Affinity Chromatograph. A Practical Approach*, 1985 eds. P. D. G. Dean, W. S. Johnson, and F. A. Middle, IRL Press, Oxford, pp.215). Apart from a direct coupling of the ligand to the solid support material, the bond can also be made via a spacer molecule. Many reagents that can be used as spacer molecules have been described. Examples include bis-oxiranes, water soluble carbodiimides, SPDP, and glutaraldehyde.

Finally, natural intermolecular interactions can be exploited to couple proteins to a solid support material, e.g., peptides containing a histidine-tag efficiently interact with materials containing nickel ions.

The recombinant retroviral vector is bound to the compound by incubating a preparation of said recombinant retroviral vector in said tissue culture dish and said hematopoietic cells of a primate are brought in close contact with said recombinant retrovirus by seeding said hematopoietic cells of a primate in said tissue culture dish, where said contact may be further enhanced by, e.g., increasing the gravitational force.

Following the transfer procedures, it is not possible to determine the gene transfer into true hematopoietic stem cells in vitro, simply because there is no assay for these cells. However, more mature progenitor cells can be tested in standard colony assays (e.g., McNiece et al., *Blood* (1988) 72:191–195; Sutherland et al., *Blood* (1989) 74:1563–1570; Breems et al., *Leukemia* (1994) 8:1095–1104). Furthermore, a candidate stem cell population can be analyzed phenotypically (Knaän-Shanzer et al., *Gene Therapy* (1996) 3:323–333). There are several ways of testing for gene transfer into these cells. When gene X encodes a selectable marker gene, clonogenic assays can be performed in the presence of a selective compound and resistant colonies can be scored to determine expression of the marker gene. If gene X encodes a molecule that can be stained with a fluorescent labeled antibody, or when the product of gene X converts a substrate into a fluorescent product, immunofluorescence or FACS analysis can be performed to demonstrate expression of the transgene. When gene X encodes a transport molecule that pumps a fluorescent substrate in or out of cells, expression of gene X can be measured by FACS analysis. Alternatively, isolated progenitor cell derived colonies or cells sorted on a FACS on the basis of their phenotype can be subjected to PCR analysis specific for the introduced retroviral vector. The latter can be done on any vector irrespective of the nature of gene X.

Several of the embodiments i–x exemplified above may be combined to further optimize the transfer of gene X into the hematopoietic cells of a primate. It is, therefore, to be understood that any combination of said embodiments is also part of the invention. All modifications within the scope of the invention that may be contemplated by the skilled artisan are also claimed to be part of the present invention. All embodiments of the method of the invention can further be used after the hematopoietic cells of a primate have been enriched for hematopoietic stem cells, which is to be preferred in some cases. Enrichment of hematopoietic cells of primates for hematopoietic stem cells can be accomplished by various methods known in the art.

Below the invention is illustrated with practical examples. It is to be understood that only certain embodiments of the invention are illustrated and that the examples should not be considered restrictive in character.

EXAMPLES

Example (a) describes the production of virus-producing cells and recombinant retroviral vectors useful in the invention. In example (b) cells and vectors of example (a) are shown to be useful for the introduction of a gene X into hematopoietic cells of primates, without affecting the in vivo regenerating capacity of the graft. Example (c1) describes a procedure for the enrichment of isolated hematopoietic cells from a primate for hematopoietic stem cells. In example (c2) the usefulness of the invention for the introduction of a gene X into enriched hematopoietic stem cells of a primate without affecting the in vivo regenerating capacity of the graft is demonstrated. Example (d) shows efficient transduction of hematopoietic stem cells of a primate by sedimentation of recombinant retroviral vectors onto said hematopoietic stem cells at increased gravitational force. Example (e 1) shows the production of peptides useful in the invention as recombinant retroviral vector binding compounds, and example (e2) describes how these peptides are used for the transfer of gene X into hematopoietic cells of a primate according to the invention. Example (f1) discloses a procedure for the establishment of a human stroma cell culture derived from the natural microenvironment present in the human bone marrow, and example (f2) describes the use of this stroma cell culture as a binding compound for the transfer of gene X into haemopoietic cells of a primate.

Example a

Production of Selectable Stable Recombinant Retrovirus-producing Cells

In this practical example, use was made of the retroviral vector construct pLgAL(ΔMo+PyF101) (Van Beusechem et al., (1990) *J. Exp. Med.* 172:729), wherein A represents the human cDNA gene coding for adenosine deaminase (ADA). Twenty micrograms of this construct were transfected to the ecotropic packaging cell line GP+E-86 (Markowitz et al., (1988) *J. Virol.* 62:1120), according to the method described by Chen and Okayama(Chen and Okayama (1987) *Mol. Cell. Biol.* 7:2745). Prior to the transfection, the GP+E-86 cells had been cultured in medium containing 15 µg/ml hypoxanthine, 250 µg/ml xanthine and 25 µg/ml mycophenolic acid, so as to select for the preservation of the DNA sequences responsible for the production of the viral proteins. Transfectants that produce a functional human ADA enzyme were isolated by means of a selective culture in medium with a combination of 4 µM xylofuranosyl-adenine (Xyl-A) and 10 nM deoxycoformycin (dCF) (Van Beusechem et al., (1990) *J. Exp. Med.* 172:729).

Then, with the thus obtained cells a ping-pong culture as described by Kozak and Kabat (Kozak and Kabat (1990) *J. Virol.* 64:3500) was initiated. To that end, 5×10$^3$ transfectants were mixed with an equal amount of GP+envAm12 amphotropic packaging cells (Markowitz et al., (1988) *Virology* 167:400) and cultured together in α-modified DMEM (Dulbecco's Modified Eagle's Medium) with 10% FCS (Fetal Calf Serum) and 8 µg/ml polybrene. The amphotropic packaging cells were also selected prior to use, for the preservation of the DNA sequences coding for the viral proteins (in the medium as described for GP+E-86 cells, with 200 µg/ml hygromycin B added thereto). The culture was expanded for two weeks, at which time the amphotropic virus-producing cells were recovered using the resistance of these cells against hygromycin B. Individual GP+envAm12 clones that express functional human ADA and produce the viral proteins, were obtained by culturing limited cell numbers in medium containing all the above-mentioned components in the amounts mentioned. In all, 12 of such clones were isolated and tested.

DNA analysis demonstrated that the clones contained several copies of the retroviral vector. The titer of the virus supernatants produced by the 12 clones was measured by exposing murine fibroblasts to dilutions of these supernatants and subsequently determining the number of fibroblasts that had acquired resistance against Xyl-A/dCF as a result thereof. The different clones produced between $3\times10^3$ and $2\times10^5$ infective virus particles per milliliter supernatant. The best clones produced 100× more virus than the best amphotropic LgAL(ΔMo+PyF101) virus-producing cell line to date, which had been obtained via a single infection with ecotropic virus.

In order to obtain some idea about the most promising clone with regard to the use in bone marrow gene therapy procedures, rhesus monkey bone marrow was cocultivated for three days with each of the 12 virus-producing cell lines. Subsequently, the preservation of the capacity of the bone marrow to form hematopoietic colonies in vitro and the infection efficiency regarding the hematopoietic precursor cells, which are at the origin of these colonies, were determined. With some of the clones, infection efficiencies of up to 40–45% Xyl-A/dCF resistant precursor cells could be achieved, while none of the clones showed a clear toxicity towards these bone marrow cells.

On the basis of all aforementioned criteria, a cell line was chosen, which was called POAM-P1. This cell line was used to demonstrate in the practical example described under b the usefulness of the thus obtained virus procedures for the genetic modification of the blood-forming organ of primates.

Two further constructs based on the pLgXL(ΔMo+PyF101) retroviral vector and including further improvements were used, wherein gene X is the gene encoding human glucocerebrosidase. These vectors were designated IG-GC-2 and IG-GC-4 and their construction is described in detail in patent application WO96/35798, the contents of which are included herein by reference. IG-GC-2 contains the full length human placental glucocerebrosidase (hGC) cDNA, whereas IG-GC-4 has a 160 nt deletion in the 3' untranslated region of the hGC cDNA. Recombinant recombinant retroviral vector-producing cell lines were generated using the PA317 cell line with amphotropic host range (Miller and Buttimore, *Mol. Cell. Biol.* 6(1986)2895–2902) and using the PG13 cell line with GaLV host range (Miller et al., *J Virol.* 65(1991)2220–2224) as described in patent application WO96/35798. The cell lines were designated PA2 (PA317 with IG-GC-2 construct), PA4 (PA317 with IG-GC-4 construct), PG2 (PG13 with IG-GC-2 construct), and PG4 (PG13 with IG-GC-4 construct).

To harvest batches of recombinant retroviral vector supernatants, T1 80 tissue culture flasks were inoculated with $1\times10^6$ virus-producing cells in 25 ml DMDM (Gibco BRL) supplemented with 10% heat-inactivated fetal bovine serum (FBS) and said cells were allowed to grow to 90–100% confluency in 4–5 days at 37° C., 10% $CO_2$ in a 100% humidified atmosphere. Next, the temperature was changed from 37° C. to 32° C. for a period of 24 hours before the medium was replaced with 50 ml fresh culture medium. After an additional culture period of 48 hours the virus supernatant was harvested, filtered through a 0.45 μm pore size filter, aliquoted and stored at −80° C. The absence of replication competent retrovirus (RCR) was tested using a $S^+/L^-$ foci test after amplification on mus dunni cells.

The recombinant retroviral vector titer issuing from the virus-producing cell lines was established on Gaucher type II fibroblasts (GM1260). GM01260 cells were seeded at a density of $10^5$ cells per 35 mm well (in 6-well plates) in culture medium further supplemented with polybrene (4 μg/ml; Sigma). Twenty-four hours later these cells were infected with 1ml of recombinant retroviral vector supernatant after which the cells were cultured and expanded for 14 days as above. Next, genomic DNA was isolated as described by Stewart et al., (Cell 38(1984)627–637). After digestion with NheI and Southern analysis using a 0.65 kb $^{32}$p-labeled NcoI-BglI hGC fragment according to standard procedures, both an hGC endogenous fragment (19 kb) and a proviral DNA fragment of either 3.4 (IG-GC2) or 3.2 kb (IG-GC4) were visible. Comparison of signal intensities between the proviral DNA fragment and the endogenous DNA fragment by ImageQuant volumetric analysis after phosphor screen autoradiography using a Molecular Dynamics PhosphorImager 400A revealed a ratio of 0.8 (PA2), 0.3 (PA4), 0.4 (PG2), and 0.2 (PG4). Since the hybridization signal of the endogenous band represents 2n DNA, on average 1.6, 0.6, 0.8, and 0.4 provirus copies per cell were present, respectively. Taking into account that the seeded GM01260 cells probably divided once before the virus supernatant was applied, approximate virus titers of $3\times10^5$, $1\times10^5$, $2\times10^5$, and $8\times10^4$ were calculated for PA2, PA4, PG2, and PG4, respectively.

Example b

Preclinical Test of a Bone Marrow Gene Therapy Procedure in Rhesus Monkeys with the Cell Line POAM-P1 Described in Example a, above Rhesus monkey bone marrow was taken by puncturing the upper legs. The bone marrow so obtained was suspended in HBSS/Hepes with 100 units heparin and 100 μg/ml DNase I. Cells having a density lower than 1.064 g/ml were obtained by successively performing a Ficoll separation and a BSA-density gradient centrifugation (Dicke et al., (1969) *Transplantation* 8:422). These operations resulted in an enrichment of the cell population for hematopoietic stem cells by a factor of 10–20. The thus obtained bone marrow cells were introduced, in a concentration of $10^6$ cells per ml, into high glucose (4.5 g/liter) α-modified DMEM, containing 5% heat-inactivated monkey serum, 15 mg/ml BSA (Bovine Serum Albumin), $1.25\times10^{-5}$ M $Na_2SeO_3$, 0.6 mg/ml iron-saturated human transferrin, 1 μg/ml of each of the following nucleosides: adenosine, 2'-deoxyadenosine, guanosine, 2'-deoxyguanosine, cytidine, 2'-deoxycytidine, thymidine and uridine, $1.5\times10^{-5}$ M linoleic acid, $1.5\times10^{-5}$ M cholesterol, $1\times10^{-4}$ M β-mercaptoethanol, 0.4 μg/ml polybrene, 100 μg/ml streptomycin, 100 U/ml penicillin and 50 ng/ml of the recombinant rhesus monkey hematopoietic growth factor IL-3 (Burger et al., (1990) *Blood* 76:2229). The thus obtained cell suspension was seeded at a concentration of $2\times10^5$ cells per $cm^2$ onto a 70–80% confluent monocellular layer of POAM-P 1 cells, which had shortly before been exposed to 20 Gray γ-radiation. The bone marrow was cocultivated with the POAM-P1 cells for 90 h at 37° C. in a moisture-saturated atmosphere of 10% $CO_2$ in air.

For the duration of the cocultivation, the rhesus monkey that had donated the bone marrow was conditioned for the autologous reception of the cocultivated bone marrow by means of total body irradiation with 10 Gray x-rays, divided over two equal fractions at an interval of 24 h, performed, respectively, 2 days and 1 day prior to the transplantation. On the day of the transplantation, the cocultivated bone marrow was harvested from the culture, including the bone marrow cells that had adhered to the POAM-P1 cells or cells that had adhered to the plastic of the culture bottle during cultivation. The latter cells were obtained by means of a trypsinization. A monocellular cell suspension was prepared in a physiological salt solution with 10 μg/ml DNase I and infused into a peripheral vein of the donor monkey.

In order to determine the in vivo regeneration capacity of the cocultivated bone marrow, use was made of the semi-quantitative assay described by Gerritsen et al., (Gerritsen et al., (1988) *Transplantation* 45:301). This method is based on the observation that the rate at which circulating red and white blood cells regenerate after transplantation of autologous bone marrow cells in lethally irradiated rhesus monkeys depends on the size of the transplant. In particular the kinetics of the appearance of the precursors of red blood cells (reticulocytes) is a good standard in this connection. By determining hematological values in the blood system of the monkeys at regular intervals after the transplantation, it could be established (using the relation described by Gerritsen) that the modified bone marrow had preserved sufficient regenerative capacity and the cocultivation therefore had no toxic side effects.

Analysis at the DNA level made it clear that long periods (up to more than a year) after the transplantation, the introduced provirus could be traced in various blood cell types (mononuclear cells and granulocytes). Especially the presence of the introduced gene in the granulocytes is considered of great importance. Since granulocytes, after being generated in the bone marrow, remain in the blood stream only a few hours before being broken down, the presence of the human ADA in these cells demonstrates that a year after transplantation the bone marrow still contains very primitive cells that give rise to the formation of ripe blood cells. Also, functional expression of the introduced human ADA gene in ripe blood cells could be demonstrated. These results constitute clear proof of the fact that through the invention described here stable genetic modification of the hematopoietic system of primates can be obtained.

Example c

Preclinical Test of a Bone Marrow Gene Therapy Procedure in Rhesus Monkeys which Utilizes Purified Hematopoietic Stem Cells c1) Enrichment of Primate Bone Marrow CD34+CD11b-stem Cells Rhesus monkey bone marrow having a density lower than 1.064 g/ml was obtained as described above under Example b. This cell population was successively depleted for cells carrying the monocytes/granulocytes-marker CD11b and enriched for cells carrying the stem cell/precursor cell-marker CD34. This was performed using immunomagnetic beads, which had been made as follows: first, tosyl-activated polystyrene magnetic beads (Dynabeads M-450; Dynal, Oslo) were incubated for 24 h in a 0.5 M borate solution pH 9.5 with 1.25 $\mu$g protein A (Pharmacia, Uppsala) per $10^6$ beads. After frequent washing in PBS containing 0.1% BSA, to the beads, now protein A-coupled, saturating concentrations of monoclonal antibodies (anti-CD11b: Mol, Coulter Clone, Hialeah, Fl; anti-CD34: ICH3, watt et al., (1987) Leukemia 1) were bound by incubating for 30 min at room temperature. Finally, the beads were frequently washed in HBSS/Hepes and stored at 4° C. until use. The bone marrow cells were incubated for 20 min at 4° C. with 7 anti-CD11b beads per cell in a concentration of 5×107 cells/ml at a maximum. Unbound CD11 b-negative cells were stripped from beads and CD11 b-positive cells bound thereto, using a magnetic particle collector (MPC; Dynal) and washed in HBSS/Hepes. The thus obtained cells were incubated for 20 min at 4° C. with 5 anti-CD34 beads per cell again in a concentration of 5×$10^7$ cells/ml at a maximum. After removal of the CD34-negative cells using the MPC, the bound CD34-positive cells were recovered by means of a competitive elution with an excess of immunoglobulins. To that end, the beads with CD34-positive cells were incubated for 1 h at 37° C. in HBSS/Hepes with 25% bovine plasma (Gibco, Paisley) and 500 U/ml heparin.

c2) Introduction of the Construct pLgAL($\Delta$Mo+PyF101) Described Under a) Into Rhesus Monkey CD34+CD 11b-Stem Cells The introduction of the human ADA gene into rhesus monkey CD34+CD11b-stem cells and the autologous transplantation procedure were performed as described under Example b above, the only difference being that the cocultivation was performed with the previously described cell line POC-1 (Van Beusechem et al., (1990) *J Exp. Med.* 172:729). As noted, this cell line is unstable and not very suitable for large-scale use. For this present experiment, use could still be made of an early passage which does not have a reduced titer.

After transplantation all blood cell types regenerated completely, which demonstrates that the gene transfer procedure can also be performed on CD34+CD11b- stem cells without toxic side effects. The presence of the provirus in mononuclear blood cells and in granulocytes could also be demonstrated in these monkeys during the entire experimental period (at this point 266 days and 280 days after transplantation in two monkeys) which is still in progress. Expression of the functional human ADA enzyme could also be demonstrated in blood cells of these monkeys. The enrichment for hematopoietic stem cells prior to the gene transfer did not have any demonstrable effect on the efficiency of the gene transfer to stem cells. This experiment therefore demonstrates that the results as described under b) can also be achieved when the bone marrow has been stripped from most riper cell types, which is preferred in some uses of genetic modification of bone marrow cells.

Example d

Introduction of the IG-GC Constructs Described under (a) Into Human CD34+ Hematopoietic Stem Cells by Increased Gravitational Force Bone marrow cells were obtained by aspiration of the iliac crest of normal healthy donors or of a patient with Non-Hodgkin Lymphoma. Mononuclear cells were obtained by Ficoll gradient separation according to standard procedures. CD34+ hematopoietic stem cells were isolated using a magnetic antibody separation system (Mini Macs, Milteny) according to the procedures supplied by the manufacturer. This procedure yielded 60–95% pure CD34+ populations with recoveries ranging from 50–90% of the CD34+ cells present in the total bone marrow aspirate.

Recombinant retroviral vector supernatant of the virus-producing cell lines PA2, PA4, PG2 and PG4 obtained as described under Example (a) was used for the transduction of the isolated human CD34+ cells. Said isolated CD34+ cells were seeded at a cell density of 1×$10^5$ cells/cm$^2$ in 24-well tissue culture plates (Greiner) in 400 $\mu$l virus supernatant supplemented with 50 ng/ml interleukin-3 (Sandoz) and 4 $\mu$g/ml protamine sulfate (Novo Nordisk Pharma). The plates were subsequently centrifuged for 2.5 hours at 1100 g at room temperature, either once or four times (once daily after refreshing the virus supernatant). After each centrifugation, the cultures were placed overnight at 37° C., 10% $CO_2$ in a 100% humidified atmosphere. In a control experiment, the cells were cultured for four days as above without the 2.5 hours centrifugation steps. Instead, the recombinant retroviral vector medium was refreshed daily after a 5 minute centrifugation of the cultures at 200 g. The theoretical multiplicity of infection of functional recombinant retroviral vector particles in the total culture medium over hematopoietic target cells at the start of the procedure after each supernatant addition was 1.2, 0.4, 0.8, and 0.3 for PA2, PA4, PG2 and PG4 virus, respectively. As a control virus preparation, culture supernatant of the IGvp010 cell line (see patent application WO6/35798) was used that contains pLgXL(ΔMo+PyF101) derived recombinant retrovirus vectors carrying the human multi-drug resistance (MDR1) gene at a titer of approximately $10^5$ particles per ml as established by vincristine resistant colony formation of human bone marrow cells.

In experiment 1, CD34+ cells from bone marrow of a non-Hodgkin lymphoma patient were transduced by four incubations with PA2, PG4, or IGvp010 virus supernatant with or without transduction enhancement by centrifugation. After the transduction procedure, transduced CD34+ cells were seeded in 1 ml DMEM (Gibco BRL) with 10% FBS supplemented with 200 ng/ml SCF, 100 ng/ml IL-6, 100 ng/ml IL-3, 100 U/ml GM-CSF, and 100 ng/ml G-CSF. After a 10 day culture period at 37° C., 10% $CO_2$ in a 100% humidified atmosphere the expanded cells, representing the mature myeloid progeny of the transduced CD34+ cell population, were washed once with PBS and lysed in buffer containing 50 mM potassium phosphate buffer, pH 6.5, 0.1% Triton X-100. Following sonication and centrifugation at 4° C., the clear supernatant was transferred to new tubes, protein concentrations were measured (DC-Biorad kit) and lysates were stored at -20° C.

Glucocerebrosidase activity was determined with either 4MU-b-glucoside (Sigma) or PNP-b- glucoside (Sigma) as artificial substrate on 20 mg total protein of transduced cells according to described procedures (Aerts et al., *Eur. J Biochem.* 150(1985)565–574; Havenga et al., *BioTechniques* 21(1996)1004–1007).

TABLE 1

Comparison of 4x supernatant transduction procedure to 4 x centrifugation enhanced transduction

| Recombinant Retrovirus Vector Supernatant | Relative hGC Activity | | PCR-positive CFU-GM | |
|---|---|---|---|---|
| | Super-natant | Centri-fugation | Supernatant | Centrifugation |
| IGvp010 (negative control) | (1) | (1) | 0/24 (0%) | 0/24 (0%) |
| PA2 hGC vector | 1 | 1 | 1/24 (4%) | 5/24 (21%) |
| PG4 hGC vector | 1.3 | 4.5 | 3/24 (13%) | 3/24 (13%) |

Table 1 shows the relative glucocerebrosidase activity data of this experiment, where the results of cells subjected to transduction with the IGvp010 retrovirus vector were set at a value of 1. As can be seen, an increase in hGC activity could not be detected following transduction with PA2 virus, with or without centrifugation. In contrast, PG4 virus transduction could be measured by functional hGC activity which was 3.5-fold increased following centrifugation (4.5 versus 1.3 in the control). Successful transduction was further confirmed by performing PCR specific for the IG-GC-2 and IG-GC-4 constructs on CFU-GM clonogenic progenitor cell derived colonies. CFU-GM were obtained by seeding 5000 transduced CD34+cells in 1 ml of methylcellulose medium with cytokines (Methocult GF H4534; Stemcell Technologies, Inc., Vancouver, Canada) in 6-well plates. After 14 days, individual colonies were picked and DNA was isolated as described (van Beusechem et al., *Proc. Natl. Acad. Sci. USA* 89(1992) 7640–7644). PCR analysis was performed on this suspension using oligonucleotide primers 5'-CAGCCCATGTTCTACCAC-3' (Seq ID No: 1) and 5'-GGATCCCTAGGCTTTTGC-3'(Seq ID No: 2 A 50 µl PCR reaction typically contained 25 pmol of each oligonucleotide, 3% DMSO, 5 µl 10-times concentrated buffer provided with the enzyme, 20 pmol dNTP, and 0.25 Units SuperTaq (Promega). The cycler program consisted of 5 min. 95° C. predenaturation followed by 26 cycles of each 45 sec. 95° C., 1 min. 54° C., 1 min. 72° C. The program was ended by an elongation step of 10 min. at 72° C. Of the PCR product, 10 µl was run on a 1.5% agarose gel, transferred to a membrane and hybridized with a 0.4 kb $^{32}$p-labeled BamHI hGC fragment according to standard procedures. As can be seen in Table 1, all transductions with hGC retrovirus vectors yielded PCR-positive colonies, whereas transductions with the MDR1 control vector did not.

In experiment 2, PA2, PA4, and PG2 recombinant retroviral vector supernatants (and IGvp010 control supernatant) were used to transduce CD34+ cells from normal healthy donor bone marrow. The centrifugation procedure was performed either once or four times on subsequent days as above. One day after the transduction procedure, CFU-GM were plated for PCR analysis as above. As can be seen in Table 2, all transductions led to high percentages of hGC-vector containing CFU-GM even after a single 2.5 hour centrifugation step.

TABLE 2

Comparison of a single centrifugation enhanced transduction procedure to four repeated centrifugation enhanced transduction procedures

| Recombinant Retrovirus Vector Supernatant | PCR-positive CFU-GM/number tested (%) | |
|---|---|---|
| | Single transduction | Four rounds of transduction |
| IGvp010 control vector | 0/20 (0%) | 0/20 (0%) |
| PA2 hGC vector | 6/20 (30%) | 5/20 (25%) |
| PA4 hGC vector | 5/20 (25%) | 6/20 (30%) |
| PG2 hGC vector | 9/20 (45%) | 10/20 (50%) |

Example e

Efficient Transfer of Gene X into Human CD34+ Hematopoietic Stem Cells Using Recombinant Retroviral Vectors Bound to a Tissue Culture Dish e1) Production of Peptides Derived from Receptors for Retroviruses (GLVR)

The Gibbon ape Leukemia Virus Receptor (GLVR) proteins are transmembrane molecules expressed on the surface of mammalian cells. Their primary function is import of inorganic phosphate and sodium. To date, two different but homologous receptors have been described by means of expression cloning of complementary DNA copies of their murine and human MRNA counterparts (Johann, et al., *J. Virol.* 66(1992)1635–1640; van Zeijl, et al., *Proc. Natl. Acad. Sci. USA* 91(1994)1168–1172; Weiss and Tailor, *Cell* 82(1995)531–533). The cDNA predicted amino acid sequences and deduced hydropathy plots suggest that both these GLVR1 and GLVR2 proteins traverse the cellular membrane 10 times and have 5 extracellular loops and 4 intracellular loops. The human GLVR1 receptor confers permissivity to Gibbon ape Leukemia Virus and Feline Leukemia Virus-B, whereas the human GLVR2 or amphotropic virus receptor confers permissivity to amphotropic Murine Leukemia Viruses carrying the 4070A or 10A1 envelope molecules. The GLVR1 homologues from different rodent species have small amino acid differences in their $4^{th}$ extracellular domain which determine virus susceptibility of a cell. Recombinant chimeras between GLVR1 and GLVR2 proteins suggest that the $4^{th}$ extracellular domain in GLVR1 is involved in virus binding and infection. Therefore, we have synthesized peptides encompassing sequences from the $4^{th}$ extracellular domain of GLVR1 and GLVR2 using Fmoc chemistry (performed under contract at Research Genetics, Inc. Huntsville, Ala., USA). The amino acid sequences of said peptides read from N-terminus to C-terminus: LVYDT-GDVSSKV (SEQ ID NO:3) and LIYKQGGVTQEA (SEQ ID NO:4) for GLVR1 and GLVR2, respectively.

For certain applications of the invention, the C-terminus of said peptides is extended with 6 Histidine-residues. This enables coupling to solid support materials via nickle molecules.

e2) The use of GLVR-peptides as Recombinant Retrovirus Vector Binding Compounds to Enhance the Transfer of Gene X into Human Hematopoietic Stem Cells Non-tissue culture dishes, i.e. culture dishes not treated to enhance cell adherence (35 mm; Greiner) are incubated for 2 hours at room temperature with 2 ml 100 $\mu$M GLVR1 or GLVR2 peptide in phosphate buffered saline (PBS). This solution was prepared from a 10 mM stock in DMSO. Next, the dishes are washed once with PBS. Two ml recombinant retrovirus supernatant harvested from the PA2 cell line and from the PG4 cell line as described under (d) is incubated at 4° C. for 2 hours on GLVR2 or GLVR1 peptide coated dishes, respectively. This procedure is repeated twice. Optionally, the thus coated dishes are washed with PBS with 1% (w/v) human serum albumin (PBS/HAS) and stored at −80° C.

Human CD34+ hematopoietic stem cells are obtained as described under Example (d) above, are suspended 1–10$^6$ cells/ml in IMDM (Gibco BRL) supplemented with 50 ng/ml interleukin-3 (Sandoz), 5% heat-inactivated autologous human serum, 4 $\mu$g/ml protamine sulfate (Novo Nordisk Pharma) and 100 U/ml penicillin (Gist-Brocades) and are cultured for 48 hours at 37° C, 10% $CO_2$ in a 100% humidified atmosphere in non-tissue culture dishes. Next, the cultured cells are placed in the GLVR peptide and recombinant retroviral vector coated dishes in their original culture medium (2 ml/dish) and cultured for another 24 hours at 37° C., 10% $CO_2$ in a 100% humidified atmosphere. After this culture, all cells including any adherent cells are harvested, washed once in PBS/HAS, and used for analysis of gene transfer or for transplantation by infusion into a peripheral vein.

Our invention shows in an example that bone marrow cells cocultivated with the virus-producing cells described here are capable of genetically modifying the hematopoietic system of primates after autologous transplantation. This modification was observed for a prolonged period in several blood cell types including granulocytes, which have a very short life time (approximately 8 hours). With the method described by us, these results can also be obtained when the bone marrow has previously been enriched for hematopoietic stem cells by removal of most other (riper) bone marrow cells. These data demonstrate our capacity to infect very primitive cells and show that it is possible to carry out gene therapy using such modified bone marrow cells.

Example of Enhanced Transfer of Gene X Into Human CD34+ Haemopoietic Stem Cells Using Recombinant Retrovirus Vectors in the Presence of Human Bone Marrow Stroma f1) Establishment of Human Bone Marrow Stroma Bone marrow mononuclear cells from healthy donors are obtained as described in example (d). Five×10$^7$ cells are seeded in T75 Nunclon culture flasks (Nunc, Roskilde, Denmark) in 10 ml DMEM (Gibco) supplemented with 10% heat-inactivated FCS, and cultured at 37° C., 10% $CO_2$ in a 100% humidified atmosphere. Twenty-four hours later the entire medium, including all non-adherent cells, is removed and replaced with the same medium further supplemented with 2 mM L-glutamine (Gibco), 10$^{-4}$ M $\beta$-mercaptoethanol (Merck, Darmstadt, Germany), and 10$^{-5}$M hydrocortisone (Sigma)("stroma medium"). Once a week, the stroma medium is replaced with fresh stroma medium. After 3–5 weeks, a confluent monolayer of cells is formed. Thereafter, confluent monolayers are trypsinized with Trypsin-EDTA solution (Gibco) and split 1:10 in stroma medium each time after reaching confluence. Each reseeding step is regarded as one passage and includes 3–4 cell doublings. Three individual stroma lines were established and these have now been cultured for 40, 40, and 65 passages, respectively. The three lines exhibited similar functional properties in supporting maintenance of human haemopoietic stem cells throughout the entire study, i.e., at least during the culture period ranging from passage 5 to passage 30.

f2) The Use of Human Bone Marrow Stroma as a Binding Compound to Enhance the Retroviral Vector-mediated Transfer of Gene X into Human Haemopoietic Stem Cells Twenty-four-well tissue culture plates are precoated with 0.3% gelatine (Sigma) in PBS for 16 hours at 4° C. Stroma cells are seeded 2×105 cells/well into these plates. After 1–3 days, confluent stroma monolayers are irradiated with 25 Gy $\gamma$-radiation. Immediately thereafter, the irradiated stroma monolayers are used to support retroviral vector-mediated gene transfer.

Serum-free recombinant retrovirus supernatant is harvested from the cell line IGvp010 (see Patent Application W096/35798) that produces pLgXL($\Delta$Mo+PyF101) derived recombinant retroviral vectors carrying the MDR1 gene, either in IGTM (alpha-modified DMEM containing 1.5% BSA (Sigma), 1 $\mu$g/ml of each of the nucleosides adenosine, 2'-deoxyadenosine, guanosine, 2'-deoxyguanosine, cytidine, 2'-deoxycytidine, thymidine, and uridine (all Sigma), 1.5× 10$^{-7}$ M $Na_2SeO_3$ (Sigma), 0.6 mg/ml iron-saturated transferrin (Behring, Marburg, Germany), 1.5$^{10-7}$ M linoleic acid (Sigma), 1$^{10-4}$ M 2-mercaptoethanol (Merck, Darmstadt, Germany) with 5% fetal calf serum (FCS) or in serum-free StemPro-34 SFM Complete Medium (Gibco RBL Life Technologies, Grand Island, N.Y.). The retroviral vector supernatant is flash-frozen and stored at −80° C until use.

Human CD34+bone marrow cells are obtained as described in example (d). They are suspended 1×10$^6$ cells/ml in IGvp010 supernatant in IGTM with 5% FCS or StemPro-34 SFM Complete Medium supplemented with 50 ng/ml interleukin-3 (Gist-Brocades, Delft, The Netherlands) and 1.6 $\mu$g/ml protamine HC 1 (Kabi Pharmacia, Woerden, The Netherlands) and are seeded 5×10$^5$ cells per well onto the irradiated stroma monolayers. Control cultures are started with the same cell suspensions in culture dishes without stroma monolayers. The cells are cultured for four days at 37° C., 10% $CO_2$ in a 100% humidified atmosphere, and each day the complete medium is replaced by fresh IGvp010 supernatant and supplements. On day 4, all cells are harvested by trypsinization as above, and are used for gene transfer analysis or transplantation.

For analysis of gene transfer into haemopoietic stem cell and progenitor cell populations, the cells are stained with a phycoerythrin-conjugated anti-CD34 MoAb and with a cocktail of fluorescein isothiocyanate-conjugated Moabs directed against CD38, CD33, and CD71 as described (Knaän-Shanzer et al., Gene Therapy (1996) 3:323–333). Populations of $CD34^{bright}CD33,38,71^{negative}$ cells, CD34$^{positive}$CD33,3871$^{positive}$ cells, CD34$^{negative}$CD33,38, 71$^{positive}$ cells, and CD34$^{negative}$CD33,38,71$^{negative}$ cells are each sorted separately on a FACStar Plus flow cytometer (Becton Dickinson, Mountain View, Calif.). Aliquots of the sorted samples are used for reanalysis to determine the purity of the sorted cells. The presence of the recombinant retroviral vector genome in the sorted cells is determined by a semi-quantitative PCR assay. To this end, untransduced bone marrow mononuclear cells are added to the sorted cell samples to reach a total of 106 cells per sample. The cells are pelleted by centrifugation and DNA is isolated from these cells as described (van Beusechem et al., *Proc. Natl. Acad. Sci. USA* (1992) 89:7640–7644). The isolated DNA concentration is measured using PicoGreen DNA Quantitation reagent (Molecular Probes, Eugene, OR) and of each isolate five independent titrations are prepared containing DNA equivalents down to 10 cells per sample. All samples are subjected to PCR analysis specific for the human MDR1 cDNA gene. The sequences of the primers used are: 5'-GTCACCATGGATGAGATTGAG-3' (SEQ ID NO:5) (upstream primer) and 5'-CCACGGACACTCCTACGAG-3' (SEQ ID NO:6) (downstream primer). The reaction conditions are: 10 mM Tris-HCl pH 9.0, 50 mM KCl, 0.01% (w/v) gelatin, 0.1% Triton X-100, 1.5 mM MgCl$_2$ with 200 µM of all four dNTPs, 200 pM of both primers, and 0.25U SuperTaq polymerase (HT Biotechnology Ltd. Cambridge, UK) in a total volume of 50 µl. Forty cycles of 1 minute at 94° C., 1 minute at 55° C. and 1 minute at 72° C. are performed in 96-well plates using a Biometra UNO-Thermoblock thermocycler. The reaction products are separated on 0.8% agarose gel, blotted, and subject to Southern analysis with human MDR1 gene specific probes according to standard procedures (Sambrook, Fritsch, and Maniatis (1989) *Molecular Cloning. A Laboratory Manual.* Second edition, Cold Spring Harbor Laboratory Press, Cold Spring Harbor, N.Y.). The frequency of PCR-positive cells is determined on the basis of the detection of specific amplification products in the five independent titrations. The outcome of this analysis is corrected for a possible contribution to the PCR signal by any contaminating cells with a different phenotype using the data from the FACS reanalysis of the sorted samples. (See Knaän-Shanzer et al. *Gene Therapy* (1996) 3:323–333.

Our invention shows in an example that bone marrow cells cocultivated with the virus-producing cells described here are capable of genetically modifying the hematopoietic system of primates after autologous transplantation. This modification was observed for a prolonged period in several blood cell types including granulocytes, which have a very short life time (approximately 8 hours). With the method described by us, these results can also be obtained when the bone marrow has previously been enriched for hematopoietic stem cells by removal of most other (riper) bone marrow cells. These data demonstrate our capacity to infect very primitive cells and show that it is possible to carry out gene therapy using such modified bone marrow cells.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for preparing genetically modified primate hematopoietic stem cells, said method comprising:
   a) providing isolated primate hematopoietic stem cells,
   b) co-culturing the isolated primate hematopoietic stem cells with retrovirus producer cells which produce a recombinant retroviral vector, wherein the retroviral vector contains a DNA sequence of interest,
   c) harvesting from the co-culture both non-adherent and adherent primate hematopoietic stem cells which contain the DNA sequence of interest.

2. The method according to claim 1, wherein the retroviral vector is an MuLV retroviral vector.

3. The method according to claim 2, wherein the retroviral vector comprises two LTRs from MuLV and the 5' region of the gag gene of MuLV.

4. The method according to claim 3, wherein the MuLV is Mo-MuLV and at least the 3'LTR is a hybrid LTR, where the PyF101 enhancer replaces the Mo-MuLV enhancer.

5. The method according to claim 4, wherein the retroviral vector is pLgXL(ΔMo+PyF101), where X represents the DNA sequence of interest.

6. The method according to claim 1, wherein the producer cells are mammalian cells that contain at least one packaging construct that expresses the gag, pol and env genes of MuLV.

7. The method according to claim 6, wherein the env gene is from an amphotropic MuLV.

8. The method according to claim 6, wherein the producer cells contain two different packaging constructs that together express the gag, pol and env genes of MuLV, where the constructs are contained in at least two different eukaryotic expression vectors.

9. The method according to claim 8, wherein each of the expression vectors contains a DNA sequence encoding for a selective marker.

10. The method according to claim 6, wherein the producer cells are GP+envAM12.

11. The method according to claim 1, wherein the retroviral vector is an amphotropic retroviral vector.

12. The method according to claim 11, wherein the producer cells contain more than one copy of the retroviral vector integrated into the genome of each of the producer cells.

13. The method according to claim 1, wherein the co-culture is in a medium containing serum and at least one hematopoietic growth factor.

14. A method for preparing genetically modified primate hematopoietic cells, said method comprising:

a) providing isolated primate hematopoietic cells, b) co-culturing the isolated primate hematopoietic cells with retrovirus producer cells which produce a recombinant retroviral vector, wherein the retroviral vector contains a DNA sequence of interest, c) harvesting from the co-culture both non-adherent and adherent primate hematopoietic cells which contain the DNA sequence of interest.

* * * * *

UNITED STATES PATENT AND TRADEMARK OFFICE
CERTIFICATE OF CORRECTION

PATENT NO.      : 6,472,212 B1
DATED           : October 29, 2002
INVENTOR(S)     : Domenico Valerio and Victor Willem van Beusechem It is certified that error appears in the above-identified patent and that said Letters Patent is hereby corrected as shown below:

Title page,
Item [75], change "Van" to -- van --
Item [57], ABSTRACT,
Line 4, after "retroviral" insert -- particles, --

Column 1,
Line 10, change "antional" to -- national --
Line 50, change "226:41 0;" to -- 226:410; --

Column 2,
Line 35, change "1:1 1 1)" to -- 1:111) --

Column 8,
Line 3, change "preferred" (first occurrence) to -- are used --

Column 10,
Line 9, change "omithine" to -- ornithine --

Column 11,
Line 7, change "VII" to -- VIII --

Column 13,
Line 4, before "selected" delete "be"

Column 16,
Line 18, insert a period after "g"
Line 63, before "includes" change "an" to -- and --

Column 20,
Line 48, change "01. M" to -- 0.1M --
Line 49, change "Tris-HC 1" to -- Tris-HC1 --

Column 23,
Lines 36-37, delete "recombinant"
Line 47, change "T1 80" to -- T180 --

Column 24,
Line 50, change "POAM-P 1" to -- POAM-P1 --

UNITED STATES PATENT AND TRADEMARK OFFICE
CERTIFICATE OF CORRECTION

PATENT NO. : 6,472,212 B1
DATED : October 29, 2002
INVENTOR(S) : Domenico Valerio and Victor Willem van Beusechem It is certified that error appears in the above-identified patent and that said Letters Patent is hereby corrected as shown below:

Column 25,
Line 55, change "1)" to -- 1:417) --
Line 59, change "107" to -- $10^7$ --

Column 29,
Line 36, change "1-$10^6$" to -- 1 x $10^6$ --
Lines 51-63, delete the lines in their entirety
Line 64, change "Example of" to -- Example f -- and move "Example f" to its own line centered above the line beginning "Enhanced Transfer" and below the line ending "peripheral vein."

Column 30,
Line 27, change "105" to -- $10^5$ --
Line 41, change "$1.5^{10-7}$" to -- 1.5 x $10^{-7}$ --
Line 42, change "$1^{10-4}$" to -- 1 x $10^{-4}$ --
Line 44, change "RBL" to -- BRL --
Line 52, change "HC 1" to -- HC1 --

Column 31,
Line 1, insert a comma after "38"
Line 10, change "106" to -- $10^6$ --

Signed and Sealed this

Seventh Day of October, 2003

JAMES E. ROGAN
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<221> NAME/KEY: misc_feature
<223> OTHER INFORMATION: Description of Artificial Sequence: primer
      specific for the IG-GC-2 and IG-GC-4 constructs which contain the
      full length human placental glucocerebrosidase (hGC) cDNA and the
      hGC cDNA with 160 nucleotide deletion in the 3' region,
      respectively

<400> SEQUENCE: 1
cagcccatgt tctaccac                                                 18

<210> SEQ ID NO 2
<211> LENGTH: 18
<212> TYPE: DNA
<213> ORGANISM: Artificial Sequence
<220> FEATURE:
<221> NAME/KEY: misc_feature
<223> OTHER INFORMATION: Description of Artificial Sequence: primer
      specific for the IG-GC-2 and IG-GC-4 constructs which contain the
      full length human placental glucocerebrosidase (hGC) cDNA and the
      hGC cDNA with 160 nucleotide deletion in the 3' region,
      respectively

<400> SEQUENCE: 2
```

```
ggatccctag gcttttgc                                                        18

<210> SEQ ID NO 3
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on the 4th extracellular domain of Gibbon ape Leukemia Virus
      Receptor protein 1.

<400> SEQUENCE: 3

Leu Val Tyr Asp Thr Gly Asp Val Ser Ser Lys Val
1               5                   10

<210> SEQ ID NO 4
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: peptide
      based on the 4th extracellular domain of Gibbon ape Leukemia Virus
      Receptor protein 2.

<400> SEQUENCE: 4

Leu Ile Tyr Lys Gln Gly Gly Val Thr Gln Glu Ala
1               5                   10

<210> SEQ ID NO 5
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence: primer
      specific for the human multi drug resistance gene 1 (MDR1) cDNA

<400> SEQUENCE: 5
gtcaccatgg atgagattga g                                                    21

<210> SEQ ID NO 6
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial Sequence: primer
      specific for the human multi drug resistance gene 1 (MDR1) cDNA

<400> SEQUENCE: 6
ccacggacac tcctacgag                                                       19
```